(12) United States Patent
Eckhardt et al.

(10) Patent No.: US 7,560,450 B2
(45) Date of Patent: Jul. 14, 2009

(54) XANTHINE DERIVATIVES, THE PREPARATION THEREOF AND THEIR USE AS PHARMACEUTICAL COMPOSITIONS

(75) Inventors: Matthias Eckhardt, Biberach (DE); Frank Himmelsbach, Mittelbiberach (DE); Elke Langkopf, Warthausen (DE); Roland Maier, Biberach (DE); Michael Mark, Biberach (DE); Mohammad Tadayyon, Ulm (DE)

(73) Assignee: Boehringer Ingelheim Pharma GmbH & Co., KG, Ingelheim (DE)

( * ) Notice: Subject to any disclaimer, the term of this patent is extended or adjusted under 35 U.S.C. 154(b) by 93 days.

(21) Appl. No.: 10/716,141

(22) Filed: Nov. 18, 2003

(65) Prior Publication Data

US 2004/0138215 A1    Jul. 15, 2004

Related U.S. Application Data

(60) Provisional application No. 60/432,450, filed on Dec. 11, 2002.

(30) Foreign Application Priority Data

Nov. 21, 2002    (DE)  ................................. 102 54 304

(51) Int. Cl.
| | |
|---|---|
| *C07D 473/06* | (2006.01) |
| *A61K 31/522* | (2006.01) |
| *A61P 3/10* | (2006.01) |
| *A61P 3/04* | (2006.01) |

(52) U.S. Cl. .................. 514/211.08; 544/268; 544/269; 544/270; 544/271; 544/272; 544/267; 544/235; 544/237; 544/105; 544/182; 544/212; 544/118; 514/217.06; 514/230.5; 514/249; 514/252.02; 514/263.2; 514/263.21; 514/263.22; 514/263.23; 514/263.35; 514/263.36; 514/242; 514/245; 540/575; 540/600

(58) Field of Classification Search ................ 544/118, 544/268, 269, 270, 271, 272, 267, 235, 237; 544/105, 182, 212; 540/575.6, 575, 600; 514/263.36, 263.35, 263.23, 263.22, 263.2, 514/211.08, 217.06, 242, 245, 263.21, 230.5, 514/249, 250.02, 252.02

See application file for complete search history.

(56) References Cited

U.S. PATENT DOCUMENTS

| | | | |
|---|---|---|---|
| 2,928,833 A | 3/1960 | Leake et al. | |
| 4,005,208 A | 1/1977 | Bender | |
| 4,599,338 A | 7/1986 | Regnier et al. | |
| 5,041,448 A | 8/1991 | Janssens | |
| 5,051,517 A | 9/1991 | Findeisen | |
| 5,223,499 A | 6/1993 | Greenlee | |
| 5,234,897 A | 8/1993 | Findeisen et al. | |
| 5,258,380 A | 11/1993 | Janssens | |
| 5,266,555 A | 11/1993 | Findeisen et al. | |
| 5,389,642 A | 2/1995 | Dorsch | |
| 5,470,579 A | 11/1995 | Bonte et al. | |
| 5,719,279 A | 2/1998 | Kuefner-Muhl et al. | |
| 5,753,635 A | 5/1998 | Buckman | |
| 6,303,661 B1 | 10/2001 | Demuth | |
| 6,342,601 B1 | 1/2002 | Bantick | |
| 6,548,481 B1 | 4/2003 | Demuth et al. | |
| 6,579,868 B1 | 6/2003 | Asano et al. | |
| 6,784,195 B2 | 8/2004 | Hale et al. | |
| 6,821,978 B2 * | 11/2004 | Chackalamannil et al. | ............... 514/262.1 |
| 6,869,947 B2 | 3/2005 | Kanstrup | |
| 7,060,722 B2 | 6/2006 | Kitajima | |
| 7,074,794 B2 | 7/2006 | Kitajima | |
| 7,074,798 B2 | 7/2006 | Yoshikawa | |
| 7,074,923 B2 | 7/2006 | Dahanukar | |
| 7,109,192 B2 | 9/2006 | Hauel | |
| 7,179,809 B2 | 2/2007 | Eckhardt | |
| 7,183,280 B2 | 2/2007 | Himmelsbach | |
| 7,192,952 B2 | 3/2007 | Kanstrup | |
| 7,217,711 B2 | 5/2007 | Eckhardt | |
| 7,235,538 B2 | 6/2007 | Kanstrup et al. | |
| 2002/0161001 A1 | 10/2002 | Kanstrup | |
| 2002/0169174 A1 | 11/2002 | Chackalamannil et al. | |
| 2002/0198205 A1 | 12/2002 | Himmelsbach | |
| 2003/0105077 A1 | 6/2003 | Kanstrup et al. | |
| 2003/0199528 A1 | 10/2003 | Kanstrup | |
| 2003/0232987 A1 | 12/2003 | Dahanukar et al. | |
| 2003/0236272 A1 | 12/2003 | Carr | |
| 2004/0034014 A1 | 2/2004 | Kanstrup et al. | |

(Continued)

FOREIGN PATENT DOCUMENTS

CA    2136288 A1    5/1995

(Continued)

OTHER PUBLICATIONS

International Search Report Reference No. PCT/EP 03/12821.

(Continued)

*Primary Examiner*—Mark L Berch
(74) *Attorney, Agent, or Firm*—Michael P. Morris; Mary-Ellen M. Devlin; David L. Kershner

(57) ABSTRACT

The present invention relates to substituted xanthines of general formula (I)

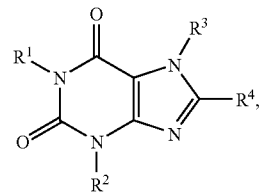

the tautomers, the stereoisomers, the mixtures thereof, the prodrugs thereof and the salts thereof, which have valuable pharmacological properties, particularly an inhibitory effect on the activity of the enzyme dipeptidylpeptidase-IV (DPP-IV).

15 Claims, No Drawings

U.S. PATENT DOCUMENTS

| | | | |
|---|---|---|---|
| 2004/0077645 A1 | 4/2004 | Himmelsbach et al. | |
| 2004/0082570 A1* | 4/2004 | Yoshikawa et al. | 514/218 |
| 2004/0087587 A1 | 5/2004 | Himmelsbach | |
| 2004/0097510 A1* | 5/2004 | Himmelsbach et al. | 514/248 |
| 2004/0116328 A1 | 6/2004 | Yoshikawa et al. | |
| 2004/0122228 A1* | 6/2004 | Maier et al. | 544/117 |
| 2004/0138214 A1* | 7/2004 | Himmelsbach et al. | 514/230.5 |
| 2004/0138215 A1 | 7/2004 | Eckhardt | |
| 2004/0166125 A1* | 8/2004 | Himmelsbach et al. | 424/400 |
| 2005/0020574 A1 | 1/2005 | Hauel et al. | |
| 2005/0026921 A1 | 2/2005 | Eckhardt | |
| 2005/0130985 A1 | 6/2005 | Himmelsbach | |
| 2005/0171093 A1 | 8/2005 | Eckhardt et al. | |
| 2005/0187227 A1 | 8/2005 | Himmelsbach et al. | |
| 2005/0203095 A1 | 9/2005 | Eckhardt | |
| 2005/0234108 A1 | 10/2005 | Himmelsbach et al. | |
| 2005/0261352 A1 | 11/2005 | Eckhardt | |
| 2006/0004074 A1 | 1/2006 | Eckhardt | |
| 2006/0058323 A1 | 3/2006 | Eckhardt et al. | |
| 2006/0063787 A1 | 3/2006 | Yoshikawa | |
| 2006/0079541 A1* | 4/2006 | Langkopf et al. | 514/263.35 |
| 2006/0094722 A1 | 5/2006 | Yasuda | |
| 2006/0100199 A1 | 5/2006 | Yoshikawa et al. | |
| 2006/0142310 A1 | 6/2006 | Pfrengle et al. | |
| 2006/0173056 A1 | 8/2006 | Kitajima | |
| 2006/0205711 A1 | 9/2006 | Himmelsbach | |
| 2006/0247226 A1 | 11/2006 | Himmelsbach | |
| 2007/0027168 A1 | 2/2007 | Pfrengle et al. | |
| 2007/0088038 A1 | 4/2007 | Eckhardt | |
| 2007/0093659 A1 | 4/2007 | Bonfanti | |
| 2007/0142383 A1 | 6/2007 | Eckhardt | |
| 2007/0185091 A1* | 8/2007 | Himmelsbach et al. | 514/217.06 |
| 2007/0219178 A1 | 9/2007 | Muramoto | |
| 2007/0259900 A1 | 11/2007 | Sieger | |
| 2007/0281940 A1 | 12/2007 | Dugi | |

FOREIGN PATENT DOCUMENTS

| | | |
|---|---|---|
| CA | 2418656 A1 | 2/2002 |
| CA | 2496325 A1 | 3/2004 |
| CA | 2496249 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2590912 A1 | 6/2006 |
| DE | 10109021 A1 | 9/2002 |
| DE | 10117803 A1 | 10/2002 |
| EP | 0149578 A2 | 7/1985 |
| EP | 0400974 A2 | 5/1990 |
| EP | 0399285 A1 | 11/1990 |
| EP | 0412358 A1 | 2/1991 |
| EP | 0524482 A1 | 1/1993 |
| EP | 0657454 A1 | 6/1995 |
| EP | 1054012 A1 | 11/2000 |
| EP | 1338595 A2 | 8/2003 |
| EP | 1514552 A1 | 3/2005 |
| EP | 1537880 A1 | 8/2005 |
| ES | 385302 A1 | 4/1973 |
| FR | 2707641 A1 | 1/1995 |
| JP | S37-4895 | 6/1962 |
| JP | 2003/300977 | 10/2003 |
| JP | 2006/045146 | 2/2006 |
| JP | 2006/045156 | 2/2006 |
| WO | 91/07945 A1 | 6/1991 |
| WO | 94/03456 A1 | 2/1994 |
| WO | 99/29695 A1 | 6/1999 |
| WO | WO 02/02560 A2 | 1/2002 |
| WO | 02/14271 A1 | 2/2002 |
| WO | WO 02/24698 A1 | 3/2002 |
| WO | WO 02/068420 A1 | 9/2002 |
| WO | WO 03/004496 A1 | 1/2003 |
| WO | 03/024965 A2 | 3/2003 |
| WO | 03/057200 A2 | 7/2003 |
| WO | WO 03/104229 A1 | 12/2003 |
| WO | 2004/018467 A2 | 3/2004 |
| WO | 2004/018468 A2 | 3/2004 |
| WO | 2004/028524 A1 | 4/2004 |
| WO | 2004/033455 A2 | 4/2004 |
| WO | 2004/041820 A1 | 5/2004 |
| WO | 2004/046148 A1 | 6/2004 |
| WO | 2004/048379 A1 | 6/2004 |
| WO | 2004/096806 A1 | 11/2004 |
| WO | 2004/108730 A1 | 12/2004 |
| WO | 2004/050658 A1 | 6/2005 |
| WO | 2005/058901 A1 | 6/2005 |
| WO | 2005/082906 A1 | 9/2005 |
| WO | 2005/085246 A1 | 9/2005 |
| WO | 2004/111051 A1 | 12/2005 |
| WO | 2006/029769 A1 | 3/2006 |
| WO | 2006/048427 A1 | 5/2006 |
| WO | 2006/068163 A1 | 6/2006 |
| WO | 2007/017423 A2 | 2/2007 |
| WO | 2008/017670 A1 | 2/2008 |

OTHER PUBLICATIONS

U.S. Appl. No. 11/744,700, filed May 4, 2007, Sieger.

U.S. Appl. No. 11/744,701, filed May 4, 2007, Kohlrausch.

Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.

Beljean-Leymarie et al., Hydrazines et hydrazones hétérocycliques. IV. Synthèses de dérivés de l'hydrazine dans la série des imidazo[4,5-d]pyridazinones-4, Can. J. Chem., vol. 61, No. 11, 1983, pp. 2563-2566.

Bollag, R.J. et al; "Osteoblast-Derived Cells Express Functional Glucose-Dependent Insulinotropic Peptide Receptors," Endocrinology, vol. 141, No. 3, 2000, pp. 1228-1235.

Brittain, H.G., "Methods for the Characterization of Polymorphs: X-Ray Powder Diffraction," Polymorphism in Pharmaceutical Solids, 1999, p. 235-238.

Busso et al., "Circulating CD26 is Negatively Associated with Inflammation in Human and Experimental Arthritis," Am. J. Path., vol. 166, No. 2, Feb. 2005, pp. 433-442.

Caira, M.R., "Crystalline polymorphism of organic compounds" Topics in Current Chemistry, Springer, Berlin, vol. 198, 1998, p. 163-208.

Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.

Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.

DeMeester, I. et al.; "CD26, let it cut or cut it down", Review: Immunology Today; Aug. 1999, vol. 20, No. 8 pp. 367-375.

Korom, S. et al; Inhibition of CD26/dipeptidyl peptidase IV activity in vivo prolongs cardiac allograft survival in rat recipients[1,2], Transplantation, May 27, 1997, vol. 63, No. 10, pp. 1495-1500.

Pospisilik, et al; Dipeptidyl Peptidase IV Inhibitor Treatment Stimulates β-Cell Survival and Islet Neogenesis in Streptozotocin-Induced Diabetic Rats; Diabetes, vol. 52, Mar. 2003 pp. 741-750.

Rhee et al.: "Nitrogen-15-Labeled Deoxynucleosides. 3. Synthesis of [3-$^{15}$N]-2'-Deoxyadenosine" J. Am. Chem. Soc. 1990, 112, 8174-8175.

Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.

Tanaka, S.. et al; "Suppression of Arthritis by the Inhibitors of Dipeptidyl Peptidase IV," In. J. Immunopharmac., vol. 19, No. 1, pp. 15-24, 1997.

Wolff, M.E.: "Burger's Medicinal Chemistry and Drug Discovery" Fifth Edition, vol. 1: Principles and Practice, pp. 975-977, 1994, John Wiley & Sons, Inc.

Zhong, Qing et al; "Glucose-dependent insulinotropic peptide stimulates proliferation and TGF-β release from MG-63 cells," Peptides 24 (2003) 611-616.

Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Farmatsevtichnii Zhurnal, 1986, (Kiev), vol. 5, 1986, pp. 41-44.

Chemical Abstracts Accession No. 106:95577 Romanenko et al., "Synthesis and biological activity of 3-methyl, 7-or 8-alkyl-7,8-dialkyl, heterocyclic, and cyclohexylaminoxanthines," Zaporozh. Med. Institute (1986).

Yoshikawa, Seiji et al.: Chemical Abstract of Japanese Patent No. WO 2003/104229 Preparation of purinone derivatives as dipeptidylpeptidase IV (DPP-IV) inhibitors 2003.

International Search Report for PCT/EP03/09127 mailed Nov. 28, 2003.

International Search Report for PCT/EP03/13648 mailed Apr. 5, 2004.

International Search Report for PCT/EP2007/054270 mailed Aug. 14, 2007.

International Search Report for PCT/EP2007/058181 mailed Nov. 28, 2007.

International Search Report for PCT/EP2007/054204 mailed Aug. 3, 2007.

International Search Report for PCT/EP2007/054201 mailed Aug. 29, 2007.

U.S. Appl. No. 11/744,701, filed May 4, 2007, Kohlrausch.

Patani George A. et al.: "Bioisoterism : A Rational Approach in Drug Design", Chemical Reviews, 1996, vol. 96, No. 8, pp. 3147-3176.

Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.

Januvia; Patient Information; Oct. 2007.

Zejc, Alfred et al; Badania Nad Piperazynowymi Pochodnymi Dwumetyloksantyn; Acta Polon. Pharm. XXXV. Nr 4, 1976, pp. 417-421.

* cited by examiner

XANTHINE DERIVATIVES, THE PREPARATION THEREOF AND THEIR USE AS PHARMACEUTICAL COMPOSITIONS

RELATED APPLICATIONS

The priority benefit of DE 102 54 304.6, filed Nov. 21, 2002 and U.S. Provisional Application No. 60/432,450, filed Dec. 11, 2002 are hereby claimed, both of which are incorporated by reference herein.

DETAILED DESCRIPTION

The present invention relates to new substituted xanthines of general formula

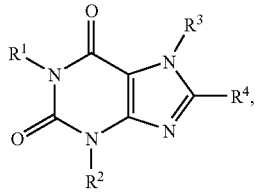

(I)

the tautomers, enantiomers, diastereomers, the mixtures thereof, the prodrugs thereof and the salts thereof, particularly the physiologically acceptable salts thereof with inorganic or organic acids or bases which have valuable pharmacological properties, particularly an inhibiting effect on the activity of the enzyme dipeptidylpeptidase-IV (DPP-IV), the preparation thereof, the use thereof for the prevention or treatment of diseases or conditions associated with an increased DPP-IV activity or capable of being prevented or alleviated by reducing the DPP-IV activity, particularly type I or type II diabetes mellitus, the pharmaceutical compositions containing a compound of general formula (I) or a physiologically acceptable salt thereof as well as processes for the preparation thereof.

In the above formula I $R^1$ represents an A-B-D group wherein

A denotes a $C_{1-6}$-alkyl group substituted by a phenyl group, where the $C_{1-6}$-alkyl group may be substituted by one to twelve fluorine atoms and the phenyl ring may be substituted by the groups $R^{10}$ to $R^{14}$ and $R^{10}$ denotes a fluorine, chlorine, bromine or iodine atom,
a $C_{1-4}$-alkyl, hydroxy, or $C_{1-4}$-alkyloxy group,
a nitro, amino, $C_{1-3}$-alkylamino, di-($C_{1-3}$-alkyl)amino, cyano-$C_{1-3}$-alkylamino, [N-(cyano-$C_{1-3}$-alkyl)-N—$C_{1-3}$-alkyl-amino], $C_{1-3}$-alkyloxy-carbonyl-$C_{1-3}$-alkylamino, pyrrolidin-1-yl, piperidin-1-yl, morpholin-4-yl, piperazin-1-yl, 4-($C_{1-3}$-alkyl)-piperazin-1-yl, $C_{1-3}$-alkyl-carbonylamino, arylcarbonylamino, aryl-$C_{1-3}$-alkyl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, $C_{1-3}$-alkyl-sulphonyl-amino, bis-($C_{1-3}$-alkylsulphonyl)-amino, aminosulphonylamino, $C_{1-3}$-alkylamino-sulphonylamino, di-($C_{1-3}$-alkyl)amino-sulphonylamino, morpholin-4-yl-sulphonylamino, ($C_{1-3}$-alkylamino)thiocarbonylamino, ($C_{1-3}$-alkyloxy-carbonylamino)carbonylamino, arylsulphonylamino or aryl-$C_{1-3}$-alkyl-sulphonylamino group,
an N—($C_{1-3}$-alkyl)-$C_{1-3}$-alkyl-carbonylamino, N—($C_{1-3}$-alkyl)-arylcarbonylamino, N—($C_{1-3}$-alkyl)-aryl-$C_{1-3}$-alkyl-carbonylamino, N—($C_{1-3}$-alkyl)-$C_{1-3}$-alkyloxy-carbonyl-amino, N-(aminocarbonyl)-$C_{1-3}$-alkylamino, N—($C_{1-3}$-alkyl-aminocarbonyl)-$C_{1-3}$-alkylamino, N-[di-($C_{1-3}$-alkyl)aminocarbonyl]-$C_{1-3}$-alkylamino, N—($C_{1-3}$-alkyl)-$C_{1-3}$-alkyl-sulphonylamino, N—($C_{1-3}$-alkyl)-arylsulphonylamino, or N—($C_{1-3}$-alkyl)-aryl-$C_{1-3}$-alkyl-sulphonylamino group,
a 2-oxo-imidazolidin-1-yl, 2,4-dioxo-imidazolidin-1-yl or 2,5-dioxo-imidazolidin-1-yl group wherein the nitrogen atom in the 3 position may in each case be substituted by a methyl or ethyl group,
a cyano, carboxy, $C_{1-4}$-alkyloxy-carbonyl, aminocarbonyl, $C_{1-3}$-alkyl-amino-carbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl or 4-($C_{1-3}$-alkyl)-piperazin-1-yl-carbonyl group,
a $C_{1-3}$-alkyl-carbonyl or an arylcarbonyl group,
a carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, piperazin-1-yl-carbonyl-$C_{1-3}$-alkyl or 4-($C_{1-3}$-alkyl)-piperazin-1-yl-carbonyl-$C_{1-3}$-alkyl group,
a carboxy-$C_{1-3}$-alkyloxy, $C_{1-3}$-alkyloxy-carbonyl-$C_{1-3}$-alkyloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyloxy, piperazin-1-yl-carbonyl-$C_{1-3}$-alkyloxy or 4-($C_{1-3}$-alkyl)-piperazin-1-yl-carbonyl-$C_{1-3}$-alkyloxy group,
a hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, piperidin-1-yl-$C_{1-3}$-alkyl, morpholin-4-yl-$C_{1-3}$-alkyl, piperazin-1-yl-$C_{1-3}$-alkyl, 4-($C_{1-3}$-alkyl)-piperazin-1-yl-$C_{1-3}$-alkyl group,
a hydroxy-$C_{1-3}$-alkyloxy, $C_{1-3}$-alkyloxy-$C_{1-3}$-alkyloxy, $C_{1-3}$-alkylsulphanyl-$C_{1-3}$-alkyloxy, $C_{1-3}$-alkylsulphinyl-$C_{1-3}$-alkyloxy, $C_{1-3}$-alkylsulphonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)-amino-$C_{1-3}$-alkyloxy, pyrrolidin-1-yl-$C_{1-3}$-alkyloxy, piperidin-1-yl-$C_{1-3}$-alkyloxy, morpholin-4-yl-$C_{1-3}$-alkyloxy, piperazin-1-yl-$C_{1-3}$-alkyloxy, 4-($C_{1-3}$-alkyl)-piperazin-1-yl-$C_{1-3}$-alkyloxy group,
a mercapto, $C_{1-3}$-alkylsulphanyl, $C_{1-3}$-alkysulphinyl, arylsulphinyl, $C_{1-3}$-alkylsulphonyl, arylsulphonyl, $C_{1-3}$-alkylsulphonyloxy, arylsulphonyloxy, trifluoromethylsulphanyl, trifluoromethylsulphinyl or trifluoromethylsulphonyl group,
a sulpho, aminosulphonyl, $C_{1-3}$-alkyl-aminosulphonyl, di-($C_{1-3}$-alkyl)-amino-sulphonyl, pyrrolidin-1-yl-sulphonyl, piperidin-1-yl-sulphonyl, morpholin-4-yl-sulphonyl, piperazin-1-yl-sulphonyl or 4-($C_{1-3}$-alkyl)-piperazin-1-yl-sulphonyl group,
a methyl or methoxy group substituted by 1 to 3 fluorine atoms,
an ethyl or ethoxy group substituted by 1 to 5 fluorine atoms,
a $C_{2-4}$-alkenyl or $C_{2-4}$-alkynyl group,
a $C_{3-4}$-alkenyloxy or $C_{3-4}$-alkynyloxy group,
a $C_{3-6}$-cycloalkyl or $C_{3-6}$-cycloalkyloxy group,
a $C_{3-6}$-cycloalkyl-$C_{1-3}$-alkyl or $C_{3-6}$-cycloalkyl-$C_{1-3}$-alkyloxy group or
an aryl, aryloxy, aryl-$C_{1-3}$-alkyl or aryl-$C_{1-3}$-alkyloxy group, $R^{11}$ and $R^{12}$, which may be identical or different, in each case denote a fluorine, chlorine, bromine or iodine atom, a $C_{1-3}$-alkyl, trifluoromethyl, hydroxy or $C_{1-3}$-alkyloxy group or a cyano group, or $R^{11}$ together with $R^{12}$, if they are bound to adjacent carbon atoms, also denote a methylenedioxy, difluoromethylenedioxy, straight-chain $C_{3-5}$-alkylene or —CH═CH—CH═CH— group, while the —CH═CH—CH═CH— group may be substituted by a fluorine, chlorine or bromine atom, by a methyl, trifluoromethyl, cyano, aminocarbonyl, aminosulphonyl, methylsulphonyl, methylsulphonylamino, methoxy, difluoromethoxy or trifluoromethoxy group, and $R^{13}$ and $R^{14}$, which may be identical or different, in each case represent a fluorine, chlorine or bromine atom, a trifluoromethyl, $C_{1-3}$-alkyl or $C_{1-3}$-alkyloxy group, a phenyl group which may be substituted by the groups $R^{10}$ to $R^{14}$, where $R^{10}$ to $R^{14}$ are as hereinbefore defined, a phenyl-$C_{2-3}$-alkenyl group wherein the phenyl moiety may be substituted by the groups $R^{10}$ to $R^{14}$, where $R^{14}$ to $R^{14}$ are as hereinbefore defined, and the alkenyl group may be substituted by one to four fluorine atoms or methyl groups, while the substituents may be identical or different, a phenyl-$C_{2-3}$-alkynyl group wherein the phenyl moiety may be substituted by the groups $R^{10}$ to $R^{14}$, where $R^{10}$ to $R^{14}$ are as hereinbefore defined, a heteroaryl-$C_{1-6}$-alkyl group, while the $C_{1-6}$-alkyl group may be substituted by one to twelve fluorine atoms, a heteroaryl group, a heteroaryl-$C_{2-3}$-alkenyl group, while the alkenyl group may be substituted by one to four fluorine atoms or methyl groups, while the substituents may be identical or different, or a heteroaryl-$C_{2-3}$-alkynyl group and B denotes an E-G group wherein E is linked to the group A and E denotes an oxygen or sulphur atom, an —$NR_a$— group wherein $R_a$ denotes a hydrogen atom, a $C_{1-6}$-alkyl, $C_{3-6}$-alkenyl, $C_{3-6}$-alkynyl, $C_{3-7}$-cycloalkyl, phenyl, phenylmethyl, heteroaryl, heteroarylmethyl, amino, $C_{1-6}$-alkylamino, di-($C_{1-6}$-alkyl)amino, hydroxy, $C_{1-6}$-alkyloxy group, while the above-mentioned phenyl rings may each be substituted by the groups $R^{10}$ to $R^{11}$, while $R^{10}$ to $R^{11}$ are as hereinbefore defined, an —$NR_a$—$NR_a$— group wherein $R_a$ is as hereinbefore defined and the two groups $R_a$ may be identical or different, an —NH—NH— group wherein the two hydrogen atoms are replaced by a straight-chain $C_{3-5}$-alkylene bridge, an —O—$NR_a$— group wherein $R_a$ is as hereinbefore defined and the oxygen atom is linked to the group A and the nitrogen atom is linked to the group G, a —O—$CR_bR_c$— group wherein the oxygen atom is linked to the group A and the carbon atom is linked to the group G and wherein $R_b$ and $R_c$, which may be identical or different, denote a hydrogen or fluorine atom, a $C_{1-6}$-alkyl, $C_{3-7}$-cycloalkyl, phenyl, phenylmethyl, while the phenyl rings may each be substituted by the groups $R^{10}$ to $R^{14}$, while $R^{10}$ to $R^{14}$ are as hereinbefore defined, or a heteroaryl or heteroarylmethyl group or $R_b$ and $R_c$ together denote a straight-chain $C_{2-6}$-alkylene group, a —S—$CR_bR_c$— group wherein the sulphur atom is linked to the group A and the carbon atom is linked to the group G and $R_b$ and $R_c$, which may be identical or different, are as hereinbefore defined, a —SO—$CR_bR_c$— group wherein the sulphur atom is linked to the group A and the carbon atom is linked to the group G and $R_b$ and $R_c$, which may be identical or different, are as hereinbefore defined, a —$SO_2$—$CR_bR_c$— group wherein the sulphur atom is linked to the group A and the carbon atom is linked to the group G and $R_b$ and $R_c$, which may be identical or different, are as hereinbefore defined, or a —$NR_a$—$CR_bR_c$— group wherein the nitrogen atom is linked to the group A and the carbon atom is linked to the group G and $R_a$, $R_b$ and $R_c$, which may be identical or different, are as hereinbefore defined, and G denotes a carbonyl or thiocarbonyl group, a methylene group substituted by an imino group wherein the nitrogen atom may be substituted by a $C_{1-6}$-alkyl, $C_{3-6}$-alkenyl, $C_{3-6}$-alkynyl, $C_{3-7}$-cycloalkyl, phenyl, phenylmethyl, heteroaryl, heteroarylmethyl, amino, $C_{1-6}$-alkylamino, di-($C_{1-6}$-alkyl)amino, pyrrolidin-1-yl, piperidin-1-yl, morpholin-4-yl, $C_{1-6}$-alkyl-carbonylamino, phenylcarbonylamino, $C_{1-6}$-alkyloxy-carbonylamino, $C_{1-6}$-alkylsulphonylamino, phenylsulphonylamino, hydroxyl, $C_{1-6}$-alkyloxy, cyano or nitro group, while the above-mentioned phenyl groups may be substituted by the groups $R^{10}$ to $R^{14}$, where $R^{10}$ to $R^{14}$ are as hereinbefore defined, a 1,1-ethenylene group wherein the carbon atom in the exo position may be substituted by one or two chlorine or fluorine atoms or one or two $C_{1-6}$-alkyl, $C_{1-6}$-perfluoroalkyl, $C_{3-6}$-alkenyl, $C_{3-6}$-alkynyl, $C_{3-7}$-cycloalkyl, phenyl, phenylmethyl, heteroaryl, heteroarylmethyl, $C_{1-6}$-alkyl-carbonyl, $C_{3-7}$-cycloalkyl-carbonyl, phenylcarbonyl, heteroarylcarbonyl, carboxy, $C_{1-6}$ alkyloxy-carbonyl, aminocarbonyl, $C_{1-6}$-alkylaminocarbonyl, di-($C_{1-6}$-alkyl)aminocarbonyl, pyrrolidin-1-ylcarbonyl, piperidin-1-ylcarbonyl, morpholin-4-ylcarbonyl, phenylaminocarbonyl, heteroarylaminocarbonyl, $C_{1-6}$-alkylsulphinyl, $C_{3-7}$-cycloalkylsulphinyl, phenylsulphinyl, heteroarylsulphinyl, $C_{1-6}$-alkylsulphonyl, $C_{3-7}$-cycloalkylsulphonyl, phenylsulphonyl, heteroarylsulphonyl, cyano or nitro groups, while the substituents may be identical or different and the above-mentioned phenyl groups may be substituted by the groups $R^{10}$ to $R^{14}$, while $R^{10}$ to $R^{14}$ are as hereinbefore defined, or represent a sulphinyl or sulphonyl group, or A together with B denotes a 1,2,3,4-tetrahydroquinolinylcarbonyl, 1,2,3,4-tetrahydroisoquinolinylcarbonyl, 2,3-dihydroindolylcarbonyl or 2,3-dihydroisoindolylcarbonyl group wherein the benzo groups may in each case be substituted by the groups $R^{10}$ to $R^{13}$, while $R^{10}$ to $R^{13}$ are as hereinbefore defined and one or two carbon atoms of the benzo group may be replaced by nitrogen atoms and the alkylene moieties of the above-mentioned groups may in each case be substituted by one or two fluorine atoms, one or two methyl groups or an oxo group, while the substituents may be identical or different, and D denotes a $C_{1-6}$-alkylene group which may be substituted by one to twelve fluorine atoms, a $C_{2-3}$-alkenylene group which may be substituted by one to four fluorine atoms or methyl groups, or a propynylene group, $R^2$ denotes a hydrogen atom, a $C_{1-6}$-alkyl group, a $C_{2-4}$-alkenyl group, a $C_{3-4}$-alkynyl group, a $C_{3-6}$-cycloalkyl group, a $C_{3-6}$-cycloalkyl-$C_{1-3}$-alkyl group, a tetrahydrofuran-3-yl, tetrahydropyran-3-yl, tetrahydropyran-4-yl, tetrahydrofuranylmethyl or tetrahydropyranylmethyl group, an aryl group, an aryl-$C_{1-4}$-alkyl group, an aryl-$C_{2-3}$-alkenyl group, an arylcarbonyl-$C_{1-2}$-alkyl group, a heteroaryl-$C_{1-3}$-alkyl group, a furanylcarbonylmethyl, thienylcarbonylmethyl, thiazolylcarbonylmethyl or pyridylcarbonylmethyl group, a $C_{1-4}$-alkyl-carbonyl-$C_{1-2}$-alkyl group, a $C_{3-6}$-cycloalkyl-carbonyl-$C_{1-2}$-alkyl group, an aryl-G-$C_{1-3}$-alkyl group, while G denotes an oxygen or sulphur atom, an imino, $C_{1-3}$-alkylimino, sulphinyl or sulphonyl group, a $C_{1-4}$-alkyl group substituted by a group $R_d$, wherein
   $R_d$ denotes a cyano, carboxy, $C_{1-3}$-alkyloxy-carbonyl, aminocarbonyl, $C_{1-3}$-alkylamino-carbonyl, di-($C_{1-3}$-alkyl)-amino-carbonyl, pyrrolidin-1-ylcarbonyl, piperidin-1-ylcarbonyl, morpholin-4-ylcarbonyl, piperazin-1-ylcarbonyl, 4-methylpiperazin-1-ylcarbonyl or 4-ethylpiperazin-1-ylcarbonyl group, or a $C_{2-4}$-alkyl group substituted by a group $R_e$, where
   $R_e$ denotes a hydroxy, $C_{1-3}$-alkyloxy, amino, $C_{1-3}$-alkylamino, di-($C_{1-3}$-alkyl)-amino, pyrrolidin-1-yl, piperidin-1-yl, morpholin-4-yl, piperazin-1-yl, 4-methyl-piperazin-1-yl or 4-ethyl-piperazin-1-yl group and is isolated from the cyclic nitrogen atom in the 3 position of the xanthine structure by at least two carbon atoms, $R^3$ denotes a $C_{3-4}$-alkyl group, a $C_{1-3}$-alkyl group substituted by a group $R_f$, where
   $R_f$ denotes a $C_{3-7}$-cycloalkyl group optionally substituted by one or two $C_{1-3}$-alkyl groups or
   a $C_{5-7}$-cycloalkenyl group optionally substituted by one or two $C_{1-3}$-alkyl groups, a $C_{3-8}$-alkenyl group, a $C_{3-6}$-alkenyl group substituted by a fluorine, chlorine or bromine atom or a trifluoromethyl group, a $C_{3-8}$-alkynyl group, an aryl group or an aryl-$C_{2-4}$-alkenyl group, and $R^4$ denotes an azetidin-1-yl or pyrrolidin-1-yl group which is substituted in the 3 position by an amino, $C_{1-3}$-alkylamino or a di-($C_{1-3}$-alkyl)amino group and may additionally be substituted by one or two $C_{1-3}$-alkyl groups, a piperidin-1-yl or hexahydroazepin-1-yl group which is substituted in the 3 position or in the 4 position by an amino, $C_{1-3}$-alkylamino or di-($C_{1-3}$-alkyl)amino group and may additionally be substituted by one or two $C_{1-3}$-alkyl groups, a 3-amino-piperidin-1-yl group wherein the piperidin-1-yl-moiety is additionally substituted by an aminocarbonyl, $C_{1-2}$-alkyl-aminocarbonyl, di-($C_{1-2}$-alkyl)aminocarbonyl, pyrrolidin-1-yl-carbonyl, (2-cyano-pyrrolidin-1-yl)carbonyl, thiazolidin-3-yl-carbonyl, (4-cyano-thiazolidin-3-yl) carbonyl, piperidin-1-ylcarbonyl or morpholin-4-ylcarbonyl group, a 3-amino-piperidin-1-yl group wherein the piperidin-1-yl-moiety in the 4 position or in the 5 position is additionally substituted by a hydroxy or methoxy group, a 3-amino-piperidin-1-yl group wherein the methylene group in the 2 position or in the 6 position is replaced by a carbonyl group, a piperidin-1-yl or hexahydroazepin-1-yl group substituted in the 3 position by an amino, $C_{1-3}$-alkylamino or di-($C_{1-3}$-alkyl)-amino group, wherein in each case two hydrogen atoms on the carbon skeleton of the piperidin-1-yl or hexahydroazepin-1-yl-group are replaced by a straight-chain alkylene bridge, this bridge containing 2 to 5 carbon atoms if the two hydrogen atoms are located on the same carbon atom, or 1 to 4 carbon atoms if the hydrogen atoms are located on adjacent carbon atoms, or 1 to 4 carbon atoms if the hydrogen atoms are located on carbon atoms separated by one atom, or 1 to 3 carbon atoms if the two hydrogen atoms are located on carbon atoms separated by two atoms, an azetidin-1-yl, pyrrolidin-1-yl, piperidin-1-yl or hexahydroazepin-1-yl group which is substituted by an amino-$C_{1-3}$-alkyl, $C_{1-3}$-alkylamino-$C_{1-3}$-alkyl or a di-($C_{1-3}$-alkyl)-amino-$C_{1-3}$-alkyl group, a piperazin-1-yl or [1,4]diazepan-1-yl group optionally substituted on the carbon skeleton by one or two $C_{1-3}$-alkyl groups, while in those compounds wherein
   the group E denotes an oxygen atom and the group G denotes a carbonyl group,
   the group E denotes an oxygen atom and the group G denotes a sulphonyl group,
   the group E denotes an —$NR_a$— group and the group G denotes a carbonyl group wherein $R_a$ is as hereinbefore defined,
   the group E denotes an —$NR_a$— group wherein $R_a$ is as hereinbefore defined, and the group G denotes a sulphonyl group or the group A denotes a phenyl or heteroaryl group optionally substituted by one of the above-mentioned groups and the group E denotes an oxygen atom and the group G denotes an ethenylene group,
   $R^4$ cannot represent a piperazin-1-yl or [1,4]diazepan-1-yl group optionally substituted on the carbon skeleton by one or two $C_{1-3}$-alkyl groups, a 3-imino-piperazin-1-yl, 3-imino-[1,4]diazepan-1-yl or 5-imino-[1,4]diazepan-1-yl group optionally substituted on the carbon skeleton by one or two $C_{1-3}$-alkyl groups, a [1,4]diazepan-1-yl group optionally substituted by one or two $C_{1-3}$-alkyl groups which is substituted in the 6 position by an amino group, a $C_{3-7}$-cycloalkyl group which is substituted by an amino, $C_{1-3}$-alkylamino or di-($C_{1-3}$-alkyl)-amino group, a $C_{3-7}$-cycloalkyl group which is substituted by an amino-$C_{1-3}$-alkyl, $C_{1-3}$-alkylamino-$C_{1-3}$-alkyl or a di-($C_{1-3}$-alkyl) amino-$C_{1-3}$-alkyl group, a $C_{3-7}$-cycloalkyl-$C_{1-2}$-alkyl group wherein the cycloalkyl moiety is substituted by an amino, $C_{1-3}$-alkylamino or di-($C_{1-3}$-alkyl)-amino group, a $C_{3-7}$-cycloalkyl-$C_{1-2}$-alkyl group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, a $C_{3-7}$-cycloalkylamino group wherein the cycloalkyl moiety is substituted by an amino, $C_{1-3}$-alkylamino or di-($C_{1-3}$-alkyl)-amino group, while the two nitrogen atoms on the cycloalkyl moiety are separated from one another by at least two carbon atoms, an N—($C_{3-7}$-cycloalkyl)-N—($C_{1-3}$-alkyl)-amino group wherein the cycloalkyl moiety is substituted by an amino, $C_{1-3}$-alkylamino or di-($C_{1-3}$-alkyl)-amino group, while the two nitrogen atoms on the cycloalkyl moiety are separated from one another by at least two carbon atoms, a $C_{3-7}$-cycloalkylamino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, an N—($C_{3-7}$-cycloalkyl)-N—($C_{1-3}$-alkyl)-amino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, a $C_{3-7}$-cycloalkyl-$C_{1-2}$-alkyl-amino group wherein the cycloalkyl moiety is substituted by an amino, $C_{1-3}$-alkylamino or di-($C_{1-3}$-alkyl)-amino group, an N—($C_{3-7}$-cycloalkyl-$C_{1-2}$-alkyl)-N—($C_{1-2}$-alkyl)-amino group wherein the cycloalkyl moiety is substituted by an amino, $C_{1-3}$-alkylamino or di-($C_{1-3}$-alkyl)-amino group, a $C_{3-7}$-cycloalkyl-$C_{1-2}$-alkyl-amino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, an N—($C_{3-7}$-cycloalkyl-$C_{1-2}$-alkyl)-N—($C_{1-2}$-alkyl)-amino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, a $R^{19}$—$C_{2-4}$-alkylamino group wherein $R^{19}$ is separated from the nitrogen atom of the $C_{2-4}$-alkylamino moiety by at least two carbon atoms and $R^{19}$ denotes an amino, $C_{1-3}$-alkylamino or di-($C_{1-3}$-alkyl)-amino group, an $R^{19}$—$C_{2-4}$-alkylamino group wherein the nitrogen atom of the $C_{2-4}$-alkylamino moiety is substituted by a $C_{1-3}$-alkyl group and $R^{19}$ is separated from the nitrogen atom of the $C_{2-4}$-alkylamino moiety by at least two carbon atoms, while $R^{19}$ is as hereinbefore defined, an amino group substituted by the group $R^{20}$ wherein $R^{20}$ denotes an azetidin-3-yl, azetidin-2-ylmethyl, azetidin-3-ylmethyl, pyrrolidin-3-yl, pyrrolidin-2-ylmethyl, pyrrolidin-3-ylmethyl, piperidin-3-yl, piperidin-4-yl, piperidin-2-ylmethyl, piperidin-3-ylmethyl or piperidin-4-ylmethyl group, while the groups mentioned for $R^{20}$ may in each case be substituted by one or two $C_{1-3}$-alkyl groups, an amino group substituted by the group $R^{20}$ and a $C_{1-3}$-alkyl group wherein $R^{20}$ is as hereinbefore defined, while the groups mentioned for $R^{20}$ may in each case be substituted by one or two $C_{1-3}$-alkyl groups, an $R^{19}$—$C_{3-4}$-alkyl group wherein the $C_{3-4}$-alkyl moiety is straight-chain and may additionally be substituted by one or two $C_{1-3}$-alkyl groups, while $R^{19}$ is as hereinbefore defined, a 3-amino-2-oxo-piperidin-5-yl or 3-amino-2-oxo-1-methyl-piperidin-5-yl group, a pyrrolidin-3-yl, piperidin-3-yl, piperidin-4-yl, hexahydroazepin-3-yl or hexahydroazepin-4-yl group which is substituted in the 1 position by an amino, $C_{1-3}$-alkylamino or di-($C_{1-3}$-alkyl)amino group, or an azetidin-2-yl-$C_{1-2}$-alkyl, azetidin-3-yl-$C_{1-2}$-alkyl, pyrrolidin-2-yl-$C_{1-2}$-alkyl, pyrrolidin-3-yl, pyrrolidin-3-yl-$C_{1-2}$-alkyl, piperidin-2-yl-$C_{1-2}$-alkyl, piperidin-3-yl, piperidin-3-yl-$C_{1-2}$-alkyl, piperidin-4-yl or piperidin-4-yl-$C_{1-2}$-alkyl group, while the above-mentioned groups may in each case be substituted by one or two $C_{1-3}$-alkyl groups, while by the aryl groups mentioned in the definition of the above groups are meant phenyl or naphthyl groups, which may be mono- or disubstituted by $R_h$ independently of one another, where the substituents are identical or different and $R_h$ denotes a fluorine, chlorine, bromine or iodine atom, a trifluoromethyl, cyano, nitro, amino, aminocarbonyl, aminosulphonyl, methylsulphonyl, acetylamino, methylsulphonylamino, $C_{1-4}$-alkyl, $C_{1-3}$-alkyl-carbonyl, cyclopropyl, ethenyl, ethynyl, hydroxy, $C_{1-4}$-alkyloxy, $C_{1-4}$-alkoxy-carbonyl, methylsulphinyl, phenylsulphinyl, methylsulphonyl, phenylsulphonyl, difluoromethoxy or trifluoromethoxy group, by the heteroaryl groups mentioned in the definitions of the above-mentioned groups are meant a pyrrolyl, furanyl, thienyl, pyridyl, indolyl, benzofuranyl, benzo-thiophenyl, quinolinyl or isoquinolinyl group, or a pyrrolyl, furanyl, thienyl or pyridyl group wherein one or two methyne groups are replaced by nitrogen atoms, or an indolyl, benzofuranyl, benzothiophenyl, quinolinyl or isoquinolinyl group wherein one to three methyne groups are replaced by nitrogen atoms, or a 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 3,4-dihydro-4-oxo-quinazolinyl, 1,2,3,4-tetrahydro-2,4-dioxo-quinazolinyl, 1,2-dihydro-2-oxoquinoxalinyl, 1,2,3,4-tetrahydro-2,3-dioxo-quinalinyl, 1,2-dihydro-1-oxo-phthalazinyl, 1,2,3,4-tetrahydro-1,4-dioxo-phthalazinyl, chromanyl, cumarinyl, 2,3-dihydro-benzo[1,4]dioxinyl or 3,4-dihydro-3-oxo-2H-benzo[1,4]oxazinyl group, and the above-mentioned heteroaryl groups may be mono- or disubstituted by $R_h$, while the substituents may be identical or different and $R_h$ is as hereinbefore defined, and, unless otherwise stated, the above-mentioned alkyl, alkenyl and alkynyl groups may be straight-chain or branched, the tautomers, the enantiomers, the diastereomers, the mixtures thereof, the prodrugs thereof and the salts thereof.

Compounds which contain a group that can be cleaved in vivo are prodrugs of the corresponding compounds wherein this group which can be cleaved in vivo has been cleaved.

The carboxy groups mentioned in the definition of the above-mentioned groups may be replaced by a group which can be converted into a carboxy group in vivo or by a group which is negatively charged under physiological conditions, and furthermore the amino and imino groups mentioned in the definition of the above-mentioned groups may be substituted by a group which can be cleaved in vivo. Such groups are described for example in WO 98/46576 and by N. M. Nielsen et al. in International Journal of Pharmaceutics 39, 75-85 (1987).

By a group which can be converted in vivo into a carboxy group is meant, for example, a hydroxymethyl group, a carboxy group esterified with an alcohol wherein the alcohol moiety is preferably a $C_{1-6}$-alkanol, a phenyl-$C_{1-3}$-alkanol, a $C_{3-9}$-cycloalkanol, while a $C_{5-8}$-cycloalkanol may additionally be substituted by one or two $C_{1-3}$-alkyl groups, a $C_{5-8}$-cycloalkanol wherein a methylene group in the 3 or 4 position is replaced by an oxygen atom or by an imino group optionally substituted by a $C_{1-3}$-alkyl, phenyl-$C_{1-3}$-alkyl, phenyl-$C_{1-3}$-alkyloxycarbonyl or $C_{2-6}$-alkanoyl group and the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkynol or phenyl-$C_{3-5}$-alkynol with the proviso that no bonds to the oxygen atom start from a carbon atom which carries a double or triple bond, a $C_{3-8}$-cycloalkyl-$C_{1-3}$-alkanol, a bicycloalkanol with a total of 8 to 10 carbon atoms which may additionally be substituted in the bicycloalkyl moiety by one or two $C_{1-3}$-alkyl groups, a 1,3-dihydro-3-oxo-1-isobenzofuranol or an alcohol of formula

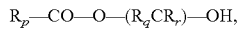

wherein
$R_p$ denotes a $C_{1-8}$-alkyl, $C_{5-7}$-cycloalkyl, $C_{1-8}$-alkyloxy, $C_{5-7}$-cycloalkyloxy, phenyl or phenyl-$C_{1-3}$-alkyl group,
$R_q$ denotes a hydrogen atom, a $C_{1-3}$-alkyl, $C_{5-7}$-cycloalkyl or phenyl group and $R_r$ denotes a hydrogen atom or a $C_{1-3}$-alkyl group, by a group which is negatively charged under physiological conditions is meant, for example, a tetrazol-5-yl, phenylcarbonylaminocarbonyl, trifluoromethylcarbonylaminocarbonyl, $C_{1-6}$-alkylsulphonylamino, phenylsulphonylamino, benzylsulphonylamino, trifluoromethylsulphonylamino, $C_{1-6}$-alkylsulphonylaminocarbonyl, phenylsulphonylaminocarbonyl, benzylsulphonylaminocarbonyl or perfluoro-$C_{1-6}$-alkylsulphonylaminocarbonyl group and by a group which can be cleaved in vivo from an imino or amino group is meant, for example, a hydroxy group, an acyl group such as a phenylcarbonyl group optionally mono- or disubstituted by fluorine, chlorine, bromine or iodine atoms, by $C_{1-3}$-alkyl or $C_{1-3}$-alkyloxy groups, while the substituents may be identical or different, a pyridinoyl group or a $C_{1-16}$-alkanoyl group such as the formyl, acetyl, propionyl, butanoyl, pentanoyl or hexanoyl group, a 3,3,3-trichloropropionyl or allyloxycarbonyl group, a $C_{1-16}$-alkyloxycarbonyl or $C_{1-16}$-alkylcarbonyloxy group, wherein hydrogen atoms may be wholly or partially replaced by fluorine or chlorine atoms such as the methoxycarbonyl, ethoxycarbonyl, propoxycarbonyl, isopropoxycarbonyl, butoxycarbonyl, tert.butoxycarbonyl, pentoxycarbonyl, hexoxycarbonyl, octyloxycarbonyl, nonyloxycarbonyl, decyloxycarbonyl, undecyloxycarbonyl, dodecyloxycarbonyl, hexadecyloxycarbonyl, methylcarbonyloxy, ethylcarbonyloxy, 2,2,2-trichloro-ethylcarbonyloxy, propylcarbonyloxy, isopropylcarbonyloxy, butylcarbonyloxy, tert.butylcarbonyloxy, pentylcarbonyloxy, hexylcarbonyloxy, octylcarbonyloxy, nonylcarbonyloxy, decylcarbonyloxy, undecylcarbonyloxy, dodecylcarbonyloxy or hexadecylcarbonyloxy group, a phenyl-$C_{1-6}$-alkyloxycarbonyl group such as the benzyloxycarbonyl, phenylethoxycarbonyl or phenylpropoxycarbonyl group, a 3-amino-propionyl group wherein the amino group may be mono- or disubstituted by $C_{1-6}$-alkyl or $C_{3-7}$-cycloalkyl groups and the substituents may be identical or different, a $C_{1-3}$-alkylsulphonyl-$C_{2-4}$-alkyloxycarbonyl, $C_{1-3}$-alkyloxy-$C_{2-4}$-alkyloxy-$C_{2-4}$-alkyloxycarbonyl, $R_pCO$—O—($R_q$ $CR_r$)—O—CO, $C_{1-6}$alkyl-CO—NH—($R_sCR_t$)—O—CO or $C_1$-alkyl-CO—O—($R_sCR_t$)—($R_sCR_t$)—O—CO group, wherein $R_p$ to $R_r$ are as hereinbefore defined,
$R_s$ and $R_t$, which may be identical or different, denote hydrogen atoms or $C_{1-3}$-alkyl groups.
Moreover, the saturated alkyl and alkyloxy moieties which contain more than 2 carbon atoms mentioned in the foregoing definitions and those that follow, unless otherwise stated, also include the branched isomers thereof such as, for example, the isopropyl, tert.butyl, isobutyl group, etc.
Preferred compounds of general formula I are those wherein
$R^1$, $R^2$ and $R^3$ are as hereinbefore defined and
$R^4$ denotes a pyrrolidin-1-yl group which is substituted in the 3 position by an amino group,
a piperidin-1-yl group which is substituted in the 3 position by an amino group,
a hexahydroazepin-1-yl-group which is substituted in the 3 position or in the 4 position by an amino group,
a (2-aminocyclohexyl)amino group,
a cyclohexyl group which is substituted in the 3 position by an amino group, or
an N-(2-aminoethyl)-N-methylamino or an N-(2-aminoethyl)-N-ethylamino group,
while, unless otherwise mentioned, the above-mentioned alkyl, alkenyl and alkynyl groups may be straight-chain or branched,
the tautomers, the enantiomers, the diastereomers, the mixtures thereof and the salts thereof.
Particularly preferred are those compounds of general formula I wherein
$R^1$ denotes an A-B-D group wherein
A denotes a phenyl, phenylmethyl, 1-phenylethyl, pyridinyl, pyridinylmethyl, 1-pyridinylethyl, pyrimidinyl, pyrimidinylmethyl, pyrazinyl, pyrazinylmethyl, 1,3,5-triazinyl, 1,3,5-triazinylmethyl, 1,2,4-triazinyl, 1,2,4-triazinylmethyl, furanyl, thienyl, pyrrolyl, imidazolyl, 1,3-oxazolyl group, while the above-mentioned phenyl and heteroaryl groups may be substituted by a fluorine, chlorine or bromine atom or by a $C_{1-4}$-alkyl, $C_{1-4}$-alkoxy, trifluoromethyl, cyano, $C_{1-3}$-alkyl-carbonyl, $C_{1-4}$-alkoxy-carbonyl, methylsulphinyl, phenylsulphinyl, methylsulphonyl, phenylsulphonyl, amino or nitro group and may optionally additionally be substituted by a fluorine, chlorine or bromine atom or by a $C_{1-4}$-alkyl, $C_{1-4}$-alkoxy, trifluoromethyl or cyano group, while the substituents may be identical or different, and
B denotes an E-G group wherein E is linked to the group A and
E denotes an oxygen atom, an —NH—, —N(CH$_3$)— or —NH—NH— group or a —OCH$_2$— group wherein the oxygen atom is linked to the group A and the carbon atom is linked to the group G, and
G denotes a carbonyl group,
a cyanoiminomethylene or nitroiminomethylene group or a 1,1-ethenylene group wherein the carbon atom in the exo position may be substituted by one or two trifluoromethyl, cyano, nitro, $C_{1-3}$-alkyloxy-carbonyl, $C_{1-4}$-alkyl-carbonyl, phenylcarbonyl, $C_{1-3}$-alkylsulphinyl, phenylsulphinyl, $C_{1-3}$-alkylsulphonyl or phenylsulphonyl groups, while the substituents may be identical or different and the above-mentioned phenyl groups may be substituted by one or two fluorine, chlorine or bromine atoms or one or two $C_{1-3}$-alkyl, trifluoromethyl, $C_{1-3}$-alkoxy, cyano, $C_{1-3}$-alkyl-carbonyl, $C_{1-3}$-alkoxy-carbonyl, methylsulphinyl, phenylsulphinyl, methylsulphonyl, phenylsulphonyl or nitro groups, while these substituents may also be identical or different,
or A and B together denote a 1,2,3,4-tetrahydroquinolin-1-ylcarbonyl or 1,2,3,4-tetrahydroisoquinolin-2-ylcarbonyl group and
D denotes a methylene group,
$R^2$ denotes a hydrogen atom,
or a $C_{1-3}$-alkyl group,
$R^3$ denotes a $C_{4-6}$-alkenyl group,
a 2-butyn-1-yl group or
a 1-cyclopenten-1-yl-methyl group
and
$R^4$ denotes a piperidin-1-yl group which is substituted in the 3 position by an amino group,
a hexahydroazepin-1-yl-group which is substituted in the 3 position or in the 4 position by an amino group,
a (2-aminocyclohexyl)amino group, a cyclohexyl group which is substituted in the 3 position by an amino group, or an N-(2-aminoethyl)-N-methylamino or an N-(2-aminoethyl)-N-ethylamino group, while, unless otherwise mentioned, the above-mentioned alkyl, alkenyl and alkynyl groups may be straight-chain or branched, the tautomers, the enantiomers, the diastereomers, the mixtures thereof and the salts thereof.

Most particularly preferred are those compounds of general formula I, wherein $R^1$ denotes an A-B-D group wherein A denotes a phenyl, phenylmethyl, 1-phenylethyl, pyridinyl, pyridinylmethyl, 1-pyridinylethyl, pyrimidinyl or pyrimidinylmethyl group, where the phenyl moiety may be substituted by a fluorine, chlorine or bromine atom or by a $C_{1-4}$-alkyl, trifluoromethyl, $C_{1-4}$-alkoxy, cyano, $C_{1-3}$-alkyl-carbonyl, $C_{1-4}$-alkoxy-carbonyl, methylsulphinyl, phenylsulphinyl, methylsulphonyl, phenylsulphonyl, amino or nitro group and may optionally additionally be substituted by a fluorine, chlorine or bromine atom or by a $C_{1-4}$-alkyl, trifluoromethyl, $C_{1-4}$-alkoxy or cyano group, while the substituents may be identical or different, and B denotes a E-G group wherein E is linked to the group A and E denotes an oxygen atom, an —NH— group, —N(CH$_3$)— group or —OCH$_2$—group wherein the oxygen atom is linked to the group A and the carbon atom is linked to the group G, and G denotes a carbonyl group, or A and B together denote a 1,2,3,4-tetrahydroquinolin-1-ylcarbonyl or 1,2,3,4-tetrahydroisoquinolin-2-ylcarbonyl group and D denotes a methylene group, $R^2$ denotes a methyl group, $R^3$ denotes a 2-buten-1-yl or 3-methyl-2-buten-1-yl group or a 2-butyn-1-yl group and $R^4$ denotes a (3-amino-piperidin-1-yl) group, the tautomers, the enantiomers, the diastereomers, the mixtures thereof and the salts thereof, but particularly those compounds of general formula I wherein $R^1$ denotes an A-B-D group wherein A denotes a phenyl, phenylmethyl, pyridinyl or pyridinylmethyl group wherein the phenyl rings may be substituted by an amino, methoxy, methyl, cyano or nitro group, and B denotes an E-G group wherein E is linked to the group A and E denotes an oxygen atom, an —NH— group or —OCH$_2$— group wherein the oxygen atom is linked to the group A and the carbon atom is linked to the group G, and G denotes a carbonyl group, or A and B together denote a 1,2,3,4-tetrahydroquinolin-1-ylcarbonyl or 1,2,3,4-tetrahydroisoquinolin-2-ylcarbonyl group and D denotes a methylene group, $R^2$ denotes a methyl group, $R^3$ denotes a 2-buten-1-yl or 3-methyl-2-buten-1-yl group or a 2-butyn-1-yl group and $R^4$ denotes a (3-amino-piperidin-1-yl) group, the tautomers, the enantiomers, the diastereomers, the mixtures thereof and the salts thereof.

The following compounds of general formula I are particularly preferred:

(a) 1-[(benzyloxycarbonyl)methyl]-3-methyl-7-(2-butyn-1-yl)-8-[(R)-3-amino-piperidin-1-yl]-xanthine, (b) 1-[(benzylaminocarbonyl)methyl]-3-methyl-7-(2-butyn-1-yl)-8-[(R)-3-amino-piperidin-1-yl]-xanthine, (c) 1-[(phenylaminocarbonyl)methyl]-3-methyl-7-(2-butyn-1-yl)-8-[(R)-3-amino-piperidin-1-yl]-xanthine, (d) 1-{[(pyridin-2-yl)aminocarbonyl]methyl}-3-methyl-7-(2-butyn-1-yl)-8-[(R)-3-amino-piperidin-1-yl]-xanthine, (e) 1-{[(pyridin-3-yl)methoxycarbonyl]methyl}-3-methyl-7-(2-butyn-1-yl)-8-[(R)-3-amino-piperidin-1-yl]-xanthine, (f) 1-{[(pyridin-3-yl)aminocarbonyl]methyl}-3-methyl-7-(2-butyn-1-yl)-8-[(R)-3-amino-piperidin-1-yl]-xanthine, (g) 1-{[(2-methyl-phenyl)aminocarbonyl]methyl}-3-methyl-7-(2-butyn-1-yl)-8-[(R)-3-amino-piperidin-1-yl]-xanthine, (h) 1-{[(2-nitro-phenyl)aminocarbonyl]methyl}-3-methyl-7-(2-butyn-1-yl)-8-[(R)-3-amino-piperidin-1-yl]-xanthine, (i) 1-{[(4-cyano-phenyl)aminocarbonyl]methyl}-3-methyl-7-(2-butyn-1-yl)-8-(3-amino-piperidin-1-yl)-xanthine, (j) 1-{[(2-methoxy-phenyl)aminocarbonyl]methyl}-3-methyl-7-(2-butyn-1-yl)-8-[(R)-3-amino-piperidin-1-yl]-xanthine, (k) 1-(2-oxo-3-phenoxy-propyl)-3-methyl-7-(2-butyn-1-yl)-8-(3-amino-piperidin-1-yl)-xanthine, (l) 1-[(2-amino-benzylaminocarbonyl)methyl]-3-methyl-7-(2-butyn-1-yl)-8-(3-amino-piperidin 1-yl)-xanthine, (m) 1-[2-(3,4-dihydro-1H-isoquinolin-2-yl)-2-oxo-ethyl]-3-methyl-7-(2-butyn-1-yl)-8-[(R)-3-amino-piperidin-1-yl]-xanthine, (n) 1-[2-(3,4-dihydro-2H-quinolin-1-yl)-2-oxo-ethyl]-3-methyl-7-(2-butyn-1-yl)-8-[(R)-3-amino-piperidin-1-yl]-xanthine, (o) 1-{[(3-cyano-phenyl)aminocarbonyl]methyl}-3-methyl-7-(2-butyn-1-yl)-8-(3-amino-piperidin-1-yl)-xanthine, (p) 1-[(3-methoxy-benzyloxycarbonyl)methyl]-3-methyl-7-(2-butyn-1-yl)-8-[(R)-3-amino-piperidin-1-yl]-xanthine and (q) 1-[(3-nitro-benzyloxycarbonyl)methyl]-3-methyl-7-(2-butyn-1-yl)-8-[(R)-3-amino-piperidin-1-yl]-xanthine and the salts thereof.

According to the invention the compounds of general formula I are obtained by methods known per se, for example by the following methods:

a) In order to prepare compounds of general formula I wherein $R^4$ is one of the groups mentioned hereinbefore, linked to the xanthine structure via a nitrogen atom:

reacting a compound of general formula (II)

wherein $R^1$ to $R^3$ are as hereinbefore defined and $Z^1$ denotes a leaving group such as a halogen atom, a substituted hydroxy, mercapto, sulphinyl, sulphonyl or sulphonyloxy group, such as for example a chlorine or bromine atom, a methanesulphonyl or methanesulphonyloxy group, with an amine of general formula $R^{4'}$—H, wherein $R^{4'}$ denotes one of the groups mentioned for $R^4$ hereinbefore which is linked to the xanthine structure via a nitrogen atom.

The reaction is expediently carried out in a solvent such as isopropanol, butanol, tetrahydrofuran, dioxane, dimethylformamide, dimethylsulphoxide, ethyleneglycol-monomethylether, ethyleneglycol diethylether or sulpholane, optionally in the presence of an inorganic or tertiary organic base, e.g. sodium carbonate, potassium carbonate or potassium hydroxide, a tertiary organic base, e.g. triethylamine, or in the presence of N-ethyl-diisopropylamine (Hünig base), while these organic bases may simultaneously also serve as solvent, and optionally in the presence of a reaction accelerator such as an alkali metal halide or a palladium-based catalyst at temperatures between −20 and 180° C., but preferably at temperatures between −10 and 120° C. The reaction may, however, also be carried out without a solvent or in an excess of the amine of general formula $R^{4'}$—H.

b) Deprotecting a compound of general formula

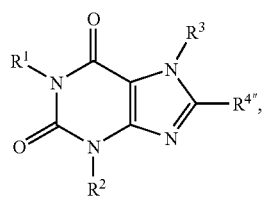

(III)

wherein $R^1$, $R^2$ and $R^3$ are as hereinbefore defined and $R^{4''}$ denotes one of the groups mentioned for $R^4$ hereinbefore which contain an imino, amino or alkylamino group, while the imino, amino or alkylamino group is substituted by a protective group, optionally followed by subsequent alkylation of the imino, amino or $C_{1-3}$-alkylamino group.

The liberating of an amino group from a protected precursor is a standard reaction in synthetic organic chemistry. There are many examples of suitable protective groups. A summary of the chemistry of protective groups can be found in Theodora W. Greene and Peter G. M. Wuts, Protective Groups in Organic Synthesis, Second Edition, 1991, published by John Wiley and Sons, and in Philip J. Kocienski, Protecting Groups, published by Georg Thieme, 1994.

The following are examples of protective groups:

the tert.-butyloxycarbonyl group which can be cleaved by treating with an acid such as for example trifluoroacetic acid or hydrochloric acid or by treating with bromotrimethylsilane or iodotrimethylsilane, optionally using a solvent such as methylene chloride, ethyl acetate, dioxane, methanol, isopropanol or diethylether at temperatures between 0° C. and 80° C., the 2,2,2-trichloroethoxycarbonyl group which can be cleaved by treating with metals such as for example zinc or cadmium in a solvent such as acetic acid or a mixture of tetrahydrofuran and a weak aqueous acid at temperatures between 0° C. and the boiling temperature of the solvent used and the carbobenzyloxycarbonyl group which can be cleaved for example by hydrogenolysis in the presence of a noble metal catalyst such as for example palladium-charcoal and a solvent such as for example alcohols, ethyl acetate, dioxane, tetrahydrofuran or mixtures of these solvents at temperatures between 0° C. and the boiling point of the solvent, by treating with boron tribromide in methylene chloride at temperatures between −20° C. and ambient temperature, or by treating with aluminium chloride/anisol at temperatures between 0° C. and ambient temperature.

A $C_{1-3}$-alkyl group may optionally be introduced subsequently by alkylation or reductive alkylation.

The subsequent alkylation is optionally carried out in a solvent or mixture of solvents such as methylene chloride, dimethylformamide, benzene, toluene, chlorobenzene, tetrahydrofuran, benzene/tetrahydrofuran or dioxane, with an alkylating agent such as a corresponding halide or sulphonic acid ester, e.g. with methyl iodide, ethyl bromide, dimethyl sulphate, optionally in the presence of a tertiary organic base or in the presence of an inorganic base, conveniently at temperatures between 0 and 150° C., preferably at temperatures between 0 and 100° C.

The subsequent reductive alkylation is carried out with a corresponding carbonyl compound such as formaldehyde, acetaldehyde, propionaldehyde or acetone in the presence of a complex metal hydride such as sodium borohydride, lithium borohydride, sodium triacetoxyborohydride or sodium cyanoborohydride conveniently at a pH of 6-7 and at ambient temperature or in the presence of a hydrogenation catalyst, e.g. with hydrogen in the presence of palladium/charcoal, at a hydrogen pressure of 1 to 5 bar. The methylation may also be carried out in the presence of formic acid as reducing agent at elevated temperatures, e.g. at temperatures between 60 and 120° C.

In the reactions described hereinbefore, any reactive groups present such as carboxy, amino, alkylamino or imino groups may be protected during the reaction by conventional protecting groups which are cleaved again after the reaction.

For example, a protecting group for a hydroxy group may be a trimethylsilyl, methyl, ethyl, tert.butyl, benzyl or tetrahydropyranyl group, protecting groups for an amino, alkylamino or imino group may be a formyl, acetyl, trifluoroacetyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl or benzyloxycarbonyl group is cleaved, for example, hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisol.

A tert.butyl or tert.butyloxycarbonyl group is preferably cleaved by treating with an acid such as trifluoroacetic acid or hydrochloric acid or by treating with iodotrimethylsilane optionally using a solvent such as methylene chloride, dioxane, methanol or diethylether.

A trifluoroacetyl group is preferably cleaved by treating with an acid such as hydrochloric acid, optionally in the presence of a solvent such as acetic acid at temperatures between 50 and 120° C. or by treating with sodium hydroxide solution optionally in the presence of a solvent such as tetrahydrofuran at temperatures between 0 and 50° C.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms racemic salts or derivatives such as e.g. esters or amides of an optically active substance, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-O-p-toluoyltartaric acid, malic acid, mandelic acid, camphorsulphonic acid, glutamic acid, aspartic acid or quinic acid. An optically active alcohol may be for example (+)- or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I thus obtained contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, etha-nolamine, diethanolamine and triethanolamine.

The compounds of general formulae II and III used as starting materials are either known from the literature or may be obtained by methods known from the literature (cf. Examples I to VIII).

As already mentioned hereinbefore, the compounds of general formula I according to the invention and the physiologically acceptable salts thereof have valuable pharmacological properties, particularly an inhibiting effect on the enzyme DPP-IV.

The biological properties of the new compounds were investigated as follows:

The ability of the substances and their corresponding salts to inhibit the DPP-IV activity can be demonstrated in a test set-up in which an extract of human colon carcinoma cell line Caco-2 is used as the DPP IV source. The differentiation of the cells in order to induce the DPP-IV expression was carried out as described by Reiher et al. in an article entitled "Increased expression of intestinal cell line Caco-2", which appeared in Proc. Natl. Acad. Sci. Vol. 90, pages 5757-5761 (1993). The cell extract was obtained from cells solubilised in a buffer (10 mM Tris HCl, 0.15 M NaCl, 0.04 t.i.u. aprotinin, 0.5% Nonidet-P40, pH 8.0) by centrifuging at 35,000 g for 30 minutes at 4° C. (to remove cell debris).

The DPP-IV assay was carried out as follows:

50 µl substrate solution (AFC; AFC is amido-4-trifluoromethylcoumarin), final concentration 100 µM, were placed in black microtitre plates. 20 µl of assay buffer (final concentrations 50 mM Tris HCl pH 7.8, 50 mM NaCl, 1% DMSO) was pipetted in. The reaction was started by adding 30 µl of solubilised Caco-2 protein (final concentration 0.14 µg of protein per well). The test substances to be investigated were typically added prediluted in 20 µl, and the volume of assay buffer was then reduced accordingly. The reaction was carried out at ambient temperature, incubating for 60 minutes. Then the fluorescence was measured in a Victor 1420 Multilabel Counter, the excitation wavelength being 405 nm and the emission wavelength being 535 nm. Blank readings (corresponding to 0% activity) were obtained in mixtures without any Caco-2 protein (volume replaced by assay buffer), control values (corresponding to 100% activity) were obtained in mixtures with no substance added. The potency of the test substances in question, expressed as $IC_{50}$ values, was calculated from dosage/activity curves consisting of 11 measuring points in each case. The following results were obtained:

| Compound (Example No.) | DPP IV inhibition $IC_{50}$ [nM] |
|---|---|
| 1 | 27 |
| 1(1) | 46 |
| 1(2) | 26 |
| 1(3) | 4 |
| 1(4) | 13 |
| 1(5) | 7 |
| 1(6) | 722 |
| 1(7) | 4 |
| 1(8) | 42 |
| 1(9) | 32 |
| 1(10) | 286 |
| 1(11) | 28 |

The compounds prepared according to the invention are well tolerated, as for example when 10 mg/kg of the compound of Example 1(3) were administered to rats by oral route no changes in the animals' behaviour could be detected.

In view of their ability to inhibit DPP-IV activity, the compounds of general formula I according to the invention and the corresponding pharmaceutically acceptable salts thereof are suitable for treating all those conditions or illnesses which can be influenced by the inhibition of the DPP-IV activity. It is therefore to be expected that the compounds according to the invention will be suitable for the prevention or treatment of diseases or conditions such as type I and type II diabetes mellitus, diabetic complications, metabolic acidosis or ketosis, insulin resistance, dyslipidaemias of various origins, arthritis, atherosclerosis and related diseases, obesity, allograft transplantation and calcitonin-induced osteoporosis. In addition these substances are capable of preventing B-cell degeneration such as e.g. apoptosis or necrosis of pancreatic B-cells. The substances are also suitable for improving or restoring the function of pancreatic cells and also increasing the number and size of pancreatic B-cells. Additionally, and on the basis of the role of the Glucagon-Like Peptides, such as e.g. GLP-1 and GLP-2 and their link with DPP-IV inhibition, it is likely that the compounds according to the invention are suitable for achieving, inter alia, a sedative or anxiety-relieving effect and also of favourably affecting catabolic states after operations or hormonal stress responses or of reducing mortality and morbidity after myocardial infarct. They are also suitable for treating all conditions which are connected with the above-mentioned effects and which are mediated by GLP-1 or GLP-2. The compounds according to the invention may also be used as diuretics or antihypertensives and are suitable for preventing and treating acute renal failure. They are also suitable for the prevention and treatment of chronic inflammatory intestinal diseases. It is also expected that DPP-IV inhibitors and hence also the compounds according to the invention may be used to treat infertility or to improve fertility in humans or mammals, particularly when the infertility is connected with insulin resistance or polycystic ovary syndrome. The substances are also suitable for treating deficiencies of growth hormone which are associated with reduced stature.

The compounds according to the invention may also be used in conjunction with other active substances. Therapeutic agents which are suitable for such combinations include, for example, antidiabetics, such as metformin, sulphonylureas (e.g. glibenclamid, tolbutamide, glimepiride), nateglinide, repaglinide, thiazolidinedione (e.g. rosiglitazone, pioglitazone), PPAR-gamma agonists (e.g. GI 262570), alpha-glucosidase inhibitors (e.g. acarbose, voglibose), alpha2 antagonists, insulin and insulin analogues, GLP-1 and GLP-1 analogues (e.g. exendin-4) or amylin. Also, inhibitors of protein tyrosine phosphatase 1, substances which influence deregulated glucose production in the liver, such as e.g. inhibitors of glucose-6-phosphatase, or fructose-1,6-bisphosphatase, glycogen phosphorylase, glucagon receptor antagonists and inhibitors of phospho-enol pyruvate carboxykinase, glycogen synthase kinase or pyruvate dehydrokinase, lipid lowering agents, such as HMG-CoA-reductase inhibitors (e.g. simvastatin, atorvastatin), fibrates (e.g. bezafibrate, fenofibrate), nicotinic acid and its derivatives, cholesterol absorption inhibitors such as for example ezetimibe, bile acid-binding substances such as for example cholestyramine, HDL-raising compounds such as for example inhibitors of CETP or regulators of ABC1 or active substances for the treatment of obesity, such as e.g. sibutramine or tetrahydrolipostatin, or $\beta_3$-agonists such as SB-418790 or AD-9677. It is also possible to combine the compounds with drugs for treating high blood pressure such as e.g. AII antagonists or ACE inhibitors, diuretics, $\beta$-blockers, etc., or combinations thereof.

The dosage required to achieve such an effect is expediently, by intravenous route, 1 to 100 mg, preferably 1 to 30 mg, and by oral route 1 to 1000 mg, preferably 1 to 100 mg, in each case 1 to 4 times a day. For this purpose, the compounds of formula I prepared according to the invention, optionally combined with other active substances, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

The Examples that follow are intended to illustrate the invention:

Preparation of the starting compounds:

EXAMPLE I

1-[(benzyloxycarbonyl)methyl]-3-methyl-7-(2-butyn-1-yl)-8-[(R)-3-(tert.-butyloxy-carbonylamino)-piperidin-1-yl]-xanthine 91 µl of benzyl chloracetate are added to 242 mg of 3-methyl-7-(2-butyn-1-yl)-8-[(R)-3-(tert.-butyloxycarbonylamino)-piperidin-1-yl]-xanthine and 110 mg potassium carbonate in 2 ml N,N-dimethylformamide and the reaction mixture is shaken for about three hours at 55° C. Then the cooled reaction mixture is combined with 5 ml methylene chloride and 15 ml of water and the organic phase is separated off. The aqueous phase is extracted with methylene chloride and the combined organic phases are dried and evaporated down.

Yield: 213 mg (65% of theory)

$R_f$ value: 0.82 (silica gel, cyclohexane/ethyl acetate=2:8)

Mass spectrum (ESI$^+$): m/z=565 [M+H]$^+$

The following compounds are obtained analogously to Example I:

(1) 1-[(benzylaminocarbonyl)methyl]-3-methyl-7-(2-butyn-1-yl)-8-[(R)-3-(tert.-butyloxycarbonylamino)-piperidin-1-yl]-xanthine Mass spectrum (ESI$^+$): m/z=564 [M+H]$^+$ (2) 1-[(phenylaminocarbonyl)methyl]-3-methyl-7-(2-butyn-1-yl)-8-[(R)-3-(tert.-butyloxycarbonylamino)-piperidin-1-yl]-xanthine $R_f$ value: 0.60 (silica gel, cyclohexane/ethyl acetate=2:8)

Mass spectrum (ESI$^+$): m/z=550 [M+H]$^+$ (3) 1-{[(pyridin-2-yl)aminocarbonyl]methyl}-3-methyl-7-(2-butyn-1-yl)-8-[(R)-3-(tert.-butyloxycarbonylamino)-piperidin-1-yl]-xanthine Mass spectrum (ESI$^+$): m/z=551 [M+H]$^+$ (4) 1-{[(pyridin-3-yl)methoxycarbonyl]methyl}-3-methyl-7-(2-butyn-1-yl)-8-[(R)-3-(tert.-butyloxycarbonylamino)-piperidin-1-yl]-xanthine Mass spectrum (ESI$^+$): m/z=566 [M+H]$^+$ (5) 1-{[(pyridin-3-yl)aminocarbonyl]methyl}-3-methyl-7-(2-butyn-1-yl)-8-[(R)-3-(tert.-butyloxycarbonylamino)-piperidin-1-yl]-xanthine Mass spectrum (ESI$^+$): m/z=551 [M+H]$^+$ (6) 1-[(2-methyl-phenylaminocarbonyl)methyl]-3-methyl-7-(2-butyn-1-yl)-8-[(R)-3-(tert.-butyloxycarbonylamino)-piperidin-1-yl]-xanthine Mass spectrum (ESI$^+$): m/z=564 [M+H]$^+$ (7) 1-[(2-nitro-phenylaminocarbonyl)methyl]-3-methyl-7-(2-butyn-1-yl)-8-[(R)-3-(tert.-butyloxycarbonylamino)-piperidin-1-yl]-xanthine Mass spectrum (ESI$^+$): m/z=595 [M+H]$^+$ (8) 1-[(4-cyano-phenylaminocarbonyl)methyl]-3-methyl-7-(2-butyn-1-yl)-8-bromo-xanthine Mass spectrum (ESI$^+$): m/z=455, 457 [M+H]$^+$ (9) 1-[(2-methoxy-phenylaminocarbonyl)methyl]-3-methyl-7-(2-butyn-1-yl)-8-[(R)-3-(tert.-butyloxycarbonylamino)-piperidin-1-yl]-xanthine Mass spectrum (ESI$^+$): m/z=580 [M+H]$^+$

(10) 1-methoxycarbonylmethyl-3-methyl-7-(2-butyn-1-yl)-8-[3-(tert.-butyloxy-carbonylamino)-piperidin-1-yl]-xanthine $R_f$ value: 0.40 (silica gel, cyclohexane/ethyl acetate=5:6)

Mass spectrum (ESI$^+$): m/z=489 [M+H]$^+$

(11) 1-methoxycarbonylmethyl-3-methyl-7-(2-butyn-1-yl)-8-[(R)-3-(tert.-butyloxy-carbonylamino)-piperidin-1-yl]-xanthine $R_f$ value: 0.82 (silica gel, methylene chloride/methanol/conc. aqueous ammonia=90:10:1)

Mass spectrum (ESI$^+$): m/z=489 [M+H]$^+$

(12) 1-[(3-cyano-phenylaminocarbonyl)methyl]-3-methyl-7-(2-butyn-1-yl)-8-bromo-xanthine Mass spectrum (ESI$^+$): m/z=455,457 [M+H]$^+$

(13) 1-[(3-methoxy-benzyloxycarbonyl)methyl]-3-methyl-7-(2-butyn-1-yl)-8-[(R)-3-(tert.-butyloxycarbonylamino)-piperidin-1-yl]-xanthine Mass spectrum (ESI$^+$): m/z=595 [M+H]$^+$

(14) 1-[(3-nitro-benzyloxycarbonyl)methyl]-3-methyl-7-(2-butyn-1-yl)-8-[(R)-3-(tert.-butyloxycarbonylamino)-piperidin-1-yl]-xanthine Mass spectrum (ESI$^+$): m/z=610 [M+H]$^+$

EXAMPLE II 3-methyl-7-(2-butyn-1-yl)-8-[(R)-3-(tert.-butyloxycarbonylamino)-piperidin-1-yl]-xanthine 11.00 g of (R)-3-tert.-butyloxycarbonylamino-piperidine are added to 15.00 g of 3-methyl-7-(2-butyn-1-yl)-8-bromo-xanthine and 16.00 g of potassium carbonate in 100 ml dimethylsulphoxide and the thick, light beige suspension is stirred for four hours at approx. 114° C. with a mechanical stirrer. Then another 900 mg of (R)-3-tert.-butyloxycarbonylamino-piperidine, dissolved in 10 ml of dimethylsulphoxide, are added to the reaction mixture which is then stirred for a further two hours at 114° C. After cooling to ambient temperature the reaction mixture is diluted with copious amounts of water. The precipitate formed is thoroughly triturated until there are no lumps remaining, and suction filtered. The light-coloured solid is again suspended with water, suction filtered, washed with water and diethyl ether and dried at 60° C. in the circulating air dryer.

Yield: 19.73 g (94% of theory)

$R_f$ value: 0.64 (silica gel, ethyl acetate)

Mass spectrum (ESI$^+$): m/z=417 [M+H]$^+$

The following compounds are obtained analogously to Example II:

(1) 1-[(4-cyano-phenylaminocarbonyl)methyl]-3-methyl-7-(2-butyn-1-yl)-8-[3-(tert.-butyloxycarbonylamino)-piperidin-1-yl]-xanthine Mass spectrum (ESI$^+$): m/z=575 [M+H]$^+$ (2) 1-(2-hydroxy-3-phenoxy-propyl)-3-methyl-7-(2-butyn-1-yl)-8-[3-(tert.-butyloxy-carbonylamino)-piperidin-1-yl]-xanthine Mass spectrum (ESI$^+$): m/z=567 [M+H]$^+$ (3) 3-methyl-7-(2-butyn-1-yl)-8-[3-(tert.-butyloxycarbonylamino)-piperidin-1-yl]-xanthine melting point: 235-237° C.

Mass spectrum (ESI$^+$): m/z=417 [M+H]$^+$ (4) 1-[(3-cyano-phenylaminocarbonyl)methyl]-3-methyl-7-(2-butyn-1-yl)-8-[3-(tert.-butyloxycarbonylamino)-piperidin-1-yl]-xanthine Mass spectrum (ESI$^+$): m/z=575 [M+H]$^+$

EXAMPLE III 3-methyl-7-(2-butyn-1-yl)-8-bromo-xanthine 17.06 g 1-bromo-2-butyn are added to 30.17 g of 3-methyl-8-bromo-xanthine and 27.00 ml of Hünig base in 370 ml of N,N-dimethylformamide. The reaction mixture is stirred for two hours at ambient temperature, then another 1 ml of 1-bromo-2-butyne and stirring is continued for a further hour at ambient temperature. For working up the reaction mixture is diluted with approx. 300 ml of water and the light-coloured precipitate formed is suction filtered and washed with water. The filter cake is washed with a little ethanol and diethyl ether and dried at 60° C. in the circulating air dryer.

Yield: 30.50 g (84% of theory)

$R_f$ value: 0.24 (silica gel, methylene chloride/methanol=95:5)

Mass spectrum (ESI$^+$): m/z=297, 299 [M+H]$^+$

EXAMPLE IV 1-(2-oxo-3-phenoxy-propyl)-3-methyl-7-(2-butyn-1-yl)-8-[3-(tert.-butyloxycarbonylamino)-piperidin-1-yl]-xanthine A solution of 107 μl dimethylsulphoxide in 0.5 ml methylene chloride is added dropwise to 64 μl oxalyl chloride in 2 ml methylene chloride with stirring at −60° C. After five minutes a solution of 345 mg of 1-(2-hydroxy-3-phenoxy-propyl)-3-methyl-7-(2-butyn-1-yl)-8-[3-(tert.-butyloxycarbonylamino)-piperidin-1-yl]-xanthine in 1.5 ml methylene chloride is added dropwise and after another 15 minutes 0.42 ml of triethylamine are added. Then the cooling bath is removed and the reaction mixture is allowed to warm up to ambient temperature. For working up it is diluted with methylene chloride and washed with water. The organic phase is dried over magnesium sulphate, evaporated down and chromatographed through a silica gel column with cyclohexane/ethyl acetate (4:1 to 1:1) as eluant.

Yield: 241 mg (70% of theory)

Mass spectrum (ESI$^+$): m/z=565 [M+H]$^+$

EXAMPLE V 1-(2-hydroxy-3-phenoxy-propyl)-3-methyl-7-(2-butyn-1-yl)-8-bromo-xanthine 556 mg of 2-phenoxymethyl-oxirane and 110 mg of potassium iodide are added to a mixture of 1.00 g 3-methyl-7-(2-butyn-1-yl)-8-bromo-xanthine and 677 mg of potassium carbonate in 25 ml of N,N-dimethylformamide. The reaction mixture is stirred for approx. eight hours at 120° C. For working up it is diluted with water and extracted with ethyl acetate. The combined extracts are dried over magnesium sulphate, evaporated down and chromatographed through a silica gel column with cyclohexane/ethyl acetate (4:1 to 1:1) as eluant.

Yield: 446 mg (30% of theory)

Mass spectrum (ESI$^+$): m/z=447, 449 [M+H]$^+$

EXAMPLE VI

1-[(2-amino-benzylaminocarbonyl)methyl]-3-methyl-7-(2-butyn-1-yl)-8-[3-(tert.-butyloxycarbonylamino)-piperidin-1-yl]-xanthine 162 mg of O-(benzotriazol-1-yl)-N,N,N',N'-tetramethyluronium tetrafluoroborate are added to a mixture of 250 mg of 1-carboxymethyl-3-methyl-7-(2-butyn-1-yl)-8-[3-(tert.-butyloxycarbonylamino)-piperidin-1-yl]-xanthine, 64 mg of 2-amino-benzylamine and 265 μl of Hünig base in 3 ml of N,N-dimethylformamide. The reaction mixture is stirred for about two hours at ambient temperature and then evaporated down. The residue is triturated with 15 ml of 1 N sodium hydroxide solution and suction filtered. The filter cake is washed with a little ethanol and diethyl ether and dried.

Yield: 228 mg (78% of theory)

$R_f$ value: 0.55 (silica gel, methylene chloride/methanol=9:1)

Mass spectrum (ESI$^+$): m/z=579 [M+H]$^+$

The following compounds are obtained analogously to Example VI:
(1) 1-[2-(3,4-dihydro-1H-isoquinolin-2-yl)-2-oxo-ethyl]-3-methyl-7-(2-butyn-1-yl)-8-[(R)-3-(tert.-butyloxycarbonylamino)-piperidin-1-yl]-xanthine $R_f$ value: 0.65 (silica gel, methylene chloride/methanol/conc. aqueous ammonia=90:10:1)

Mass spectrum (ESI$^+$): m/z=590 [M+H]$^+$ (2) 1-[2-(3,4-dihydro-2H-quinolin-1-yl)-2-oxo-ethyl]-3-methyl-7-(2-butyn-1-yl)-8-[(R)-3-(tert.-butyloxycarbonylamino)-piperidin-1-yl]-xanthine $R_f$ value: 0.70 (silica gel, methylene chloride/methanol/conc. aqueous ammonia=90:10:1)

Mass spectrum (ESI$^+$): m/z=590 [M+H]$^+$

EXAMPLE VII 1-carboxymethyl-3-methyl-7-(2-butyn-1-yl)-8-[3-(tert.-butyloxycarbonylamino)-piperidin-1-yl]-xanthine Prepared by saponifying 1-methoxycarbonylmethyl-3-methyl-7-(2-butyn-1-yl)-8-[3-(tert.-butyloxycarbonylamino)-piperidin-1-yl]-xanthine with 4 N potassium hydroxide solution in a mixture of tetrahydrofuran and methanol (5:1) at ambient temperature.

Mass spectrum (ESI$^+$): m/z=475 [M+H]$^+$

The following compounds are obtained analogously to Example VII:
(1) 1-carboxymethyl-3-methyl-7-(2-butyn-1-yl)-8-[(R)-3-(tert.-butyloxycarbonylamino)-piperidin-1-yl]-xanthine $R_f$ value: 0.23 (silica gel, methylene chloride/methanol/conc. aqueous ammonia=80:20:1)

Mass spectrum (ESI$^-$): m/z=473 [M−H]$^-$

EXAMPLE VIII (3-Methoxy-benzyl)chloroacetate 1 ml of chloroacetyl chloride is added dropwise to 1.49 ml of 3-methoxybenzyl alcohol and 1.05 ml of pyridine in 50 ml dichloromethane while cooling with an ice bath. After the addition has ended the reaction mixture is stirred for a further 30 minutes at ambient temperature. For working up it is combined with water and the aqueous phase is extracted several times with methylene chloride. The combined organic phases are dried over magnesium sulphate and evaporated down.

Yield: 2.35 g (87% of theory)

Mass spectrum (EI): m/z=214, 216 [M]$^+$

The following compounds are obtained analogously to Example VIII:
(1) (3-nitro-benzyl)-chloroacetate Mass spectrum (EI): m/z=229, 231 [M]$^+$ Preparation of the final compounds:

EXAMPLE 1

1-[(benzyloxycarbonyl)methyl]-3-methyl-7-(2-butyn-1-yl)-8-[(R)-3-amino-piperidin-1-yl]-xanthine 213 mg of 1-[(benzyloxycarbonyl)methyl]-3-methyl-7-(2-butyn-1-yl)-8-[(R)-3-(tert.-butyloxycarbonylamino)-piperidin-1-yl]-xanthine in 2 ml methylene chloride are combined with 1 ml of trifluoroacetic acid and the reaction mixture is shaken for 20 minutes at 30° C. For working up it is made alkaline with 15 ml of 1 N sodium hydroxide solution and the organic phase is separated off. The aqueous phase is extracted with methylene chloride and the combined organic phases are evaporated down. The flask residue is purified through a silica gel column with methylene chloride/methanol (100:0 to 70:30) as eluant.

Yield: 170 mg (97% of theory)

Mass spectrum (ESI$^+$): m/z=465 [M+H]$^+$

The following compounds are obtained analogously to Example 1:
(1) 1-[(benzylaminocarbonyl)methyl]-3-methyl-7-(2-butyn-1-yl)-8-[(R)-3-amino-piperidin-1-yl]-xanthine Mass spectrum (ESI$^+$): m/z=464 [M+H]$^+$ (2) 1-[(phenylaminocarbonyl)methyl]-3-methyl-7-(2-butyn-1-yl)-8-[(R)-3-amino-piperidin-1-yl]-xanthine Mass spectrum (ESI$^+$): m/z=450 [M+H]$^+$ (3) 1-{[(pyridin-2-yl)aminocarbonyl]methyl}-3-methyl-7-(2-butyn-1-yl)-8-[(R)-3-amino-piperidin-1-yl]-xanthine $R_f$ value: 0.55 (Ready-made reversed phase TLC plate (E. Merck), acetonitrile/water/trifluoroacetic acid=50:50:0.1)

Mass spectrum (ESI$^+$): m/z=451 [M+H]$^+$ (4) 1-{[(pyridin-3-yl)methoxycarbonyl]methyl}-3-methyl-7-(2-butyn-1-yl)-8-[(R)-3-amino-piperidin-1-yl]-xanthine $R_f$ value: 0.40 (silica gel, methylene chloride/methanol/triethylamine=90:10:1) Mass spectrum (ESI$^+$): m/z=466 [M+H]$^+$ (5) 1-{[(pyridin-3-yl)aminocarbonyl]methyl}-3-methyl-7-(2-butyn-1-yl)-8-[(R)-3-amino-piperidin-1-yl]-xanthine Mass spectrum (ESI$^+$): m/z=451 [M+H]$^+$ (6) 1-{[(2-methyl-phenyl)aminocarbonyl]methyl}-3-methyl-7-(2-butyn-1-yl)-8-[(R)-3-amino-piperidin-1-yl]-xanthine Mass spectrum (ESI$^+$): m/z=464 [M+H]$^+$ (7) 1-{[(2-nitro-phenyl)aminocarbonyl]methyl}-3-methyl-7-(2-butyn-1-yl)-8-[(R)-3-amino-piperidin-1-yl]-xanthine Mass spectrum (ESI$^+$): m/z=495 [M+H]$^+$ (8) 1-{[(4-cyano-phenyl)aminocarbonyl]methyl}-3-methyl-7-(2-butyn-1-yl)-8-(3-amino-piperidin-1-yl)-xanthine Mass spectrum (ESI$^+$): m/z=475 [M+H]$^+$ (9) 1-{[(2-methoxy-phenyl)aminocarbonyl]methyl}-3-methyl-7-(2-butyn-1-yl)-8-[(R)-3-amino-piperidin-1-yl]-xanthine Mass spectrum (ESI$^+$): m/z=480 [M+H]$^+$

(10) 1-(2-oxo-3-phenoxy-propyl)-3-methyl-7-(2-butyn-1-yl)-8-(3-amino-piperidin-1-yl)-xanthine Mass spectrum (ESI$^+$): m/z=465 [M+H]$^+$

(11) 1-[(2-amino-benzylaminocarbonyl)methyl]-3-methyl-7-(2-butyn-1-yl)-8-(3-amino-piperidin-1-yl)-xanthine Mass spectrum (ESI$^+$): m/z=479 [M+H]$^+$

(12) 1-[2-(3,4-dihydro-1H-isoquinolin-2-yl)-2-oxo-ethyl]-3-methyl-7-(2-butyn-1-yl)-8-[(R)-3-amino-piperidin-1-yl]-xanthine $R_f$ value: 0.15 (silica gel, methylene chloride/methanol/conc. aqueous ammonia=90:10:1)

Mass spectrum (ESI$^+$): m/z=490 [M+H]$^+$

(13) 1-[2-(3,4-dihydro-2H-quinolin-1-yl)-2-oxo-ethyl]-3-methyl-7-(2-butyn-1-yl)-8-[(R)-3-amino-piperidin-1-yl]-xanthine $R_f$ value: 0.09 (silica gel, methylene chloride/methanol/conc. aqueous ammonia=90:10:1)

Mass spectrum (ESI$^+$): m/z=490 [M+H]$^+$

(14) 1-{[(3-cyano-phenyl)aminocarbonyl]methyl}-3-methyl-7-(2-butyn-1-yl)-8-(3-amino-piperidin-1-yl)-xanthine x trifluoroacetic acid Mass spectrum (ESI$^+$): m/z=475 [M+H]$^+$

(15) 1-[(3-methoxy-benzyloxycarbonyl)methyl]-3-methyl-7-(2-butyn-1-yl)-8-[(R)-3-amino-piperidin-1-yl]-xanthine
Mass spectrum (ESI⁺): m/z=495 [M+H]⁺

(16) 1-[(3-nitro-benzyloxycarbonyl)methyl]-3-methyl-7-(2-butyn-1-yl)-8-[(R)-3-amino-piperidin-1-yl]-xanthine
Mass spectrum (ESI⁺): m/z=510 [M+H]⁺

The following compounds may also be prepared analogously to the foregoing Examples and other methods known from the literature:

(1) 1-{[(pyrimidin-2-yl)aminocarbonyl]methyl}-3-methyl-7-(2-butyn-1-yl)-8-(3-amino-piperidin-1-yl)-xanthine
(2) 1-{[(pyrimidin-4-yl)aminocarbonyl]methyl}-3-methyl-7-(2-butyn-1-yl)-8-(3-amino-piperidin-1-yl)-xanthine
(3) 1-{[(pyridin-4-yl)aminocarbonyl]methyl}-3-methyl-7-(2-butyn-1-yl)-8-(3-amino-piperidin-1-yl)-xanthine
(4) 1-{[N-(pyridin-2-yl)-N-methylaminocarbonyl]methyl}-3-methyl-7-(2-butyn-1-yl)-8-(3-amino-piperidin-1-yl)-xanthine
(5) 1-{[(4-nitrophenyl)aminocarbonyl]methyl}-3-methyl-7-(2-butyn-1-yl)-8-(3-amino-piperidin-1-yl)-xanthine
(6) 1-{[(4-cyano-2-fluorophenyl)aminocarbonyl]methyl}-3-methyl-7-(1-buten-1-yl)-8-(3-amino-piperidin-1-yl)-xanthine
(7) 1-{[(4-methylphenyl)aminocarbonyl]methyl}-3-methyl-7-(2-butyn-1-yl)-8-(3-amino-piperidin-1-yl)-xanthine
(8) 1-{[(2-cyanophenyl)aminocarbonyl]methyl}-3-methyl-7-(2-butyn-1-yl)-8-(3-amino-piperidin-1-yl)-xanthine
(9) 1-{[(3-cyano-5-chlorophenyl)aminocarbonyl]methyl}-3-methyl-7-(2-butyn-1-yl)-8-(3-amino-piperidin-1-yl)-xanthine
(10) 1-{[(pentafluorophenyl)aminocarbonyl]methyl}-3-methyl-7-(2-butyn-1-yl)-8-(3-amino-piperidin-1-yl)-xanthine
(11) 1-{[(6-cyano-2-pyridinyl)aminocarbonyl]methyl}-3-methyl-7-(3-methyl-2-buten-1-yl)-8-(3-amino-piperidin-1-yl)-xanthine
(12) 1-{[(6-methylpyridin-2-yl)aminocarbonyl]methyl}-3-methyl-7-(2-butyn-1-yl)-8-(3-amino-piperidin-1-yl)-xanthine
(13) 1-{[(5-methylpyridin-2-yl)aminocarbonyl]methyl}-3-methyl-7-(2-butyn-1-yl)-8-[N-(2-aminoethyl)-N-methylamino]-xanthine
(14) 1-{[(4-methylpyridin-2-yl)aminocarbonyl]methyl}-3-methyl-7-(2-butyn-1-yl)-8-(3-amino-piperidin-1-yl)-xanthine
(15) 1-{[(3-methylpyridin-2-yl)aminocarbonyl]methyl}-3-methyl-7-(2-butyn-1-yl)-8-(3-amino-piperidin-1-yl)-xanthine
(16) 1-{[1-(pyridin-3-yl)ethylaminocarbonyl]methyl}-3-methyl-7-(2-butyn-1-yl)-8-(3-amino-piperidin-1-yl)-xanthine
(17) 1-{[N-(pyridin-3-yl methyl)-N-methylaminocarbonyl]methyl}-3-methyl-7-(2-butyn-1-yl)-8-(3-amino-piperidin-1-yl)-xanthine
(18) 1-{[(pyridin-2-yl)methylaminocarbonyl]methyl}-3-methyl-7-(2-butyn-1-yl)-8-(3-amino-piperidin-1-yl)-xanthine
(19) 1-{[(pyridin-4-yl)methylaminocarbonyl]methyl}-3-methyl-7-(2-butyn-1-yl)-8-(3-amino-piperidin-1-yl)-xanthine
(20) 1-{[(3-cyanophenyl)methylaminocarbonyl]methyl}-3-methyl-7-(2-butyn-1-yl)-8-(3-amino-piperidin-1-yl)-xanthine
(21) 1-{[(3-nitrophenyl)methylaminocarbonyl]methyl}-3-methyl-7-(2-butyn-1-yl)-8-(3-amino-piperidin-1-yl)-xanthine
(22) 1-{[N'-(pyridin-2-yl)hydrazinocarbonyl]methyl}-3-methyl-7-(2-butyn-1-yl)-8-(3-amino-piperidin-1-yl)-xanthine
(23) 1-{[N'-(pyridin-3-yl)hydrazinocarbonyl]methyl}-3-methyl-7-(2-butyn-1-yl)-8-(3-amino-piperidin-1-yl)-xanthine
(24) 1-{[N'-(pyridin-4-yl)hydrazinocarbonyl]methyl}-3-methyl-7-(2-butyn-1-yl)-8-(3-amino-piperidin-1-yl)-xanthine
(25) 1-(phenyloxycarbonylmethyl)-3-methyl-7-(2-butyn-1-yl)-8-(3-amino-piperidin-1-yl)-xanthine
(26) 1-{[(pyridin-4-yl)methoxycarbonyl]methyl}-3-methyl-7-(3-methyl-2-buten-1-yl)-8-(3-amino-piperidin-1-yl)-xanthine
(27) 1-{[(pyridin-2-yl)methoxycarbonyl]methyl}-3-methyl-7-(2-butyn-1-yl)-8-(3-amino-piperidin-1-yl)-xanthine
(28) 1-{[(pyrimidin-5-yl)methoxycarbonyl]methyl}-3-methyl-7-(2-butyn-1-yl)-8-(3-amino-piperidin-1-yl)-xanthine
(29) 1-{[1-(2-methoxyphenyl)ethoxycarbonyl]methyl}-3-methyl-7-(2-butyn-1-yl)-8-(3-amino-piperidin-1-yl)-xanthine
(30) 1-{[(2,6-dichloro-4-trifluoromethylphenyl)methoxycarbonyl]methyl}-3-methyl-7-(2-butyn-1-yl)-8-[N-(2-aminoethyl)—N-methylamino]-xanthine
(31) 1-{[(pentafluorophenyl)methoxycarbonyl]methyl}-3-methyl-7-(2-butyn-1-yl)-8-(3-amino-piperidin-1-yl)-xanthine
(32) 1-{[(3-trifluoromethoxyphenyl}meth xycarbonyl]methyl)-3-methyl-7-(2-butyn-1-yl)-8-(3-amino-piperidin-1-yl)-xanthine
(33) 1-{[(3,5-dicyanophenyl)methoxycarbonyl]methyl}-3-methyl-7-(2-butyn-1-yl)-8-(3-amino-piperidin-1-yl)-xanthine
(34) 1-[(phenylaminomethylcarbonyl)methyl]-3-methyl-7-(2-butyn-1-yl)-8-(3-amino-piperidin-1-yl)-xanthine
(35) 1-{[(pyridin-3-yl)aminomethylcarbonyl]methyl}-3-methyl-7-(1-buten-1-yl)-8-(3-amino-piperidin-1-yl)-xanthine
(36) 1-{[(pyridin-2-yl)aminomethylcarbonyl]methyl}-3-methyl-7-(2-butyn-1-yl)-8-(3-amino-piperidin-1-yl)-xanthine
(37) 1-{[(pyridin-4-yl)aminomethylcarbonyl]methyl}-3-methyl-7-(2-butyn-1-yl)-8-(3-amino-piperidin-1-yl)-xanthine
(38) 1-{[N-(pyridin-3-yl)-N-methylaminomethylcarbonyl]methyl}-3-methyl-7-(2-butyn-1-yl)-8-(3-amino-piperidin-1-yl)-xanthine
(39) 1-{[(pentafluorophenoxy)methylcarbonyl]methyl}-3-methyl-7-(2-butyn-1-yl)-8-(3-amino-piperidin-1-yl)-xanthine
(40) 1-{[(2-nitrophenoxy)methylcarbonyl]methyl}-3-methyl-7-(3-methyl-2-buten-1-yl)-8-(3-amino-piperidin-1-yl)-xanthine
(41) 1-{[(3-methylsulphonylphenoxy)methylcarbonyl]methyl}-3-methyl-7-(2-butyn-1-yl)-8-(3-amino-piperidin-1-yl)-xanthine
(42) 1-{[(1H-pyrrol-2-yloxy)methylcarbonyl]methyl}-3-methyl-7-(2-buten-1-yl)-8-(3-amino-pyrrolidin-1-yl)-xanthine
(43) 1-{[(pyridin-3-yloxy)methylcarbonyl]methyl}-3-methyl-7-(2-butyn-1-yl)-8-(3-amino-piperidin-1-yl)-xanthine
(44) 1-{[(pyridin-2-yloxy)methylcarbonyl]methyl}-3-methyl-7-(2-butyn-1-yl)-8-(3-amino-piperidin-1-yl)-xanthine

(45) 1-{[(pyridin-4-yloxy)methylcarbonyl]methyl}-3-methyl-7-[(1-cyclopentenyl)-methyl]-8-[N-(2-aminoethyl)-N-methylamino]-xanthine
(46) 1-{[(phenylsulphanyl)methylcarbonyl]methyl}-3-methyl-7-(2-butyn-1-yl)-8-(3-amino-piperidin-1-yl)-xanthine
(47) 1-{[(phenylsulphinyl)methylcarbonyl]methyl}-3-methyl-7-(2-butyn-1-yl)-8-(3-amino-piperidin-1-yl)-xanthine
(48) 1-{[(phenylsulphonyl)methylcarbonyl]methyl}-3-methyl-7-(2-butyn-1-yl)-8-(3-amino-piperidin-1-yl)-xanthine
(49) 1-[(phenylaminothiocarbonyl)methyl]-3-methyl-7-(2-butyn-1-yl)-8-(3-amino-piperidin-1-yl)-xanthine
(50) 1-{[(pyridin-2-yl)aminothiocarbonyl]methyl}-3-methyl-7-(2-butyn-1-yl)-8-[N-(2-aminoethyl)-N-methylamino]-xanthine
(51) 1-{[(pyridin-4-yl)aminothiocarbonyl]methyl}-3-methyl-7-(2-butyn-1-yl)-8-[N-(2-aminoethyl)-N-methylamino]-xanthine
(52) 1-{[(N-(pyridin-3-yl)-N-methylaminothiocarbonyl]methyl}-3-methyl-7-(2-butyn-1-yl)-8-[N-(2-aminoethyl)—N-methylamino]-xanthine
(53) 1-{[(3-methylphenyl)aminothiocarbonyl]methyl}-3-methyl-7-(3-methyl-2-buten-1-yl)-8-(3-amino-piperidin-1-yl)-xanthine
(54) 1-{[(2-methoxyphenyl)aminothiocarbonyl]methyl}-3-methyl-7-(2-butyn-1-yl)-8-(3-amino-piperidin-1-yl)-xanthine
(55) 1-{[(4-cyanophenyl)aminothiocarbonyl]methyl}-3-methyl-7-(2-butyn-1-yl)-8-(3-amino-piperidin-1-yl)-xanthine
(56) 1-[(N-phenylcarbamimidoyl)methyl]-3-methyl-7-(2-butyn-1-yl)-8-(3-amino-piperidin-1-yl)-xanthine
(57) 1-{[N-(phenylamino)-N'-cyano-carbamimidoyl]methyl}-3-methyl-7-(2-butyn-1-yl)-8-(3-amino-piperidin-1-yl)-xanthine
(58) 1-[3-cyano-2-(phenylamino)-2-propen-1-yl]-3-methyl-7-(2-butyn-1-yl)-8-(3-amino-piperidin-1-yl)-xanthine
(59) 1-[3-cyano-2-(pyridin-2-ylamino)-2-propen-1-yl]-3-methyl-7-(2-buten-1-yl)-8-(3-amino-piperidin-1-yl)-xanthine
(60) 1-{3-cyano-2-[N-(pyridin-2-yl)-N-methylamino]-2-propen-1-yl}-3-methyl-7-(3-methyl-2-buten-1-yl)-8-(3-amino-piperidin-1-yl)-xanthine
(61) 1-[3-cyano-2-(pyridin-4-ylamino)-2-propen-1-yl]-3-methyl-7-(2-butyn-1-yl)-8-(3-amino-piperidin-1-yl)-xanthine
(62) 1-[2-(pyridin-4-ylamino)-3-trifluoromethyl-2-propen-1-yl]-3-methyl-7-(2-butyn-1-yl)-8-(3-amino-piperidin-1-yl)-xanthine
(63) 1-[3-nitro-2-(pyridin-2-ylamino)-2-propen-1-yl]-3-methyl-7-[(1-cyclopentenyl)-methyl]-8-(3-amino-piperidin-1-yl)-xanthine
(64) 1-[2-(3-cyanophenylamino)-3-methylsulphinyl-2-propen-1-yl]-3-methyl-7-[(1-cyclopentenyl)methyl]-8-(3-amino-piperidin-1-yl)-xanthine
(65) 1-[2-(pyridin-4-ylamino)-3-methylsulphonyl-2-propen-1-yl]-3-methyl-7-(2-butyn-1-yl)-8-(3-amino-piperidin-1-yl)-xanthine
(66) 1-[2-(phenylamino)-3-(pyrimidin-2-yl)-2-propen-1-yl]-3-methyl-7-(3-methyl-2-buten-1-yl)-8-(3-amino-piperidin-1-yl)-xanthine
(67) 1-[3,3-dicyano-2-(phenylamino)-2-propen-1-yl]-3-methyl-7-(2-butyn-1-yl)-8-(3-amino-piperidin-1-yl)-xanthine
(68) 1-[3-cyano-3-fluoro-2-(phenylamino)-2-propen-1-yl]-3-methyl-7-(2-butyn-1-yl)-8-(3-amino-piperidin-1-yl)-xanthine
(69) 1-[(phenylaminosulphonyl)methyl]-3-methyl-7-(2-buten-1-yl)-8-[N-(2-amino-ethyl)-N-methylamino]-xanthine
(70) 1-{[(pyridin-2-yl)aminosulphonyl]methyl}-3-methyl-7-(2-butyn-1-yl)-8-(3-amino-piperidin-1-yl)-xanthine
(71) 1-({(pyridin-3-ylmethyl)aminosulphonyl]methyl}-3-methyl-7-(2-butyn-1-yl)-8-(3-amino-piperidin-1-yl)-xanthine
(72) 1-{[N-(pyridin-3-ylmethyl)-N-methylaminosulphonyl]methyl}-3-methyl-7-(2-butyn-1-yl)-8-(3-amino-piperidin-1-yl)-xanthine
(73) 1-[(phenyloxymethylsulphinyl)methyl]-3-methyl-7-(1-buten-1-yl)-8-(3-amino-piperidin-1-yl)-xanthine
(74) 1-{[(pyridin-3-yloxy)methylsulphinyl]methyl}-3-methyl-7-(2-butyn-1-yl)-8-(3-amino-pyrrolidin-1-yl)-xanthine
(75) 1-[(phenylamino)methylsulphinylmethyl]-3-methyl-7-(2-butyn-1-yl)-8-(3-amino-piperidin-1-yl)-xanthine
(76) 1-{[(pyridin-3-ylamino)methylsulphinyl]methyl}-3-methyl-7-(3-methyl-2-buten-1-yl)-8-(3-amino-piperidin-1-yl)-xanthine
(77) 1-[(phenyloxymethylsulphonyl)methyl]-3-methyl-7-(2-buten-1-yl)-8-(3-amino-piperidin-1-yl)-xanthine
(78) 1-{[(pyridin-3-yloxy)methylsulphonyl]methyl}-3-methyl-7-(2-butyn-1-yl)-8-(3-amino-piperidin-1-yl)-xanthine
(79) 1-[(phenylaminomethylsulphonyl)methyl]-3-methyl-7-(3-methyl-2-buten-1-yl)-8-(3-amino-piperidin-1-yl)-xanthine
(80) 1-{[(pyridin-3-ylamino)methylsulphonyl]methyl}-3-methyl-7-(2-butyn-1-yl)-8-(3-amino-piperidin-1-yl)-xanthine

EXAMPLE 2

| Coated tablets containing 75 mg of active substance | |
|---|---|
| 1 tablet core contains: | |
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

Weight of core: 230 mg die: 9 mm, convex

The tablet cores thus produced are coated with a film consisting essentially of hydroxypropylmethylcellulose. The finished film-coated tablets are polished with beeswax.

Weight of coated tablet: 245 mg.

EXAMPLE 3

Tablets containing 100 mg of active substance

Composition:
1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

EXAMPLE 4

Tablets containing 150 mg of active substance

Composition:
1 tablet contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

EXAMPLE 5

Hard gelatine capsules containing 150 mg of active substance 1 capsule contains:

| | |
|---|---|
| active substance | 150.0 mg |
| corn starch (dried) | approx. 80.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

EXAMPLE 6

Suppositories containing 150 mg of active substance 1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE 7

Suspension containing 50 mg of active substance 100 ml of suspension contain:

| | | |
|---|---|---|
| active substance | 1.00 | g |
| carboxymethylcellulose-Na-salt | 0.10 | g |
| methyl p-hydroxybenzoate | 0.05 | g |
| propyl p-hydroxybenzoate | 0.01 | g |
| glucose | 10.00 | g |
| glycerol | 5.00 | g |
| 70% sorbitol solution | 20.00 | g |
| flavouring | 0.30 | g |
| dist. water | ad 100 | ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 8

Ampoules containing 10 mg active substance

Composition:

| active substance | 10.0 mg |
| 0.01 N hydrochloric acid | q.s. |
| double-distilled water | ad 2.0 ml |

Preparation:

The active substance is dissolved in the necessary amount of 0.01 N HCl, made isotonic with common salt, filtered sterile and transferred into 2 ml ampoules.

EXAMPLE 9

Ampoules containing 50 mg of active substance

Composition:

| active substance | 50.0 mg |
| 0.01 N hydrochloric acid | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A compound of formula

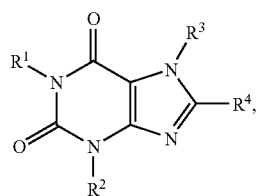

(I)

wherein $R^1$ represents an A-B-D group wherein (I) A denotes (a) a $C_{1-6}$-alkyl group substituted by a phenyl group, where the $C_{1-6}$-alkyl group may be substituted by one to twelve fluorine atoms and the phenyl ring may be substituted by the groups $R^{10}$ to $R^{14}$ and i. $R^{10}$ denotes a. a fluorine, chlorine, bromine or iodine atom, b. a $C_{1-4}$-alkyl, hydroxy, or $C_{1-4}$-alkyloxy group, c. a nitro, amino, $C_{1-3}$-alkylamino, di-($C_{1-3}$-alkyl)amino, cyano-$C_{1-3}$-alkylamino, [N-(cyano-$C_{1-3}$-alkyl)-N—$C_{1-3}$-alkyl-amino], $C_{1-3}$-alkyloxy-carbonyl-$C_{1-3}$-alkylamino, pyrrolidin-1-yl, piperidin-1-yl, morpholin-4-yl, piperazin-1-yl, 4-($C_{1-3}$-alkyl)-piperazin-1-yl, $C_{1-3}$-alkyl-carbonylamino, arylcarbonylamino, aryl-$C_{1-3}$-alkyl-carbonylamino, $C_{1-3}$-alkyloxy-carbonylamino, aminocarbonylamino, $C_{1-3}$-alkyl-amino-carbonylamino, di-($C_{1-3}$-alkyl)aminocarbonylamino, $C_{1-3}$-alkyl-sulphonylamino, bis-($C_{1-3}$-alkylsulphonyl)-amino, aminosulphonylamino, $C_{1-3}$-alkylamino-sulphonylamino, di-($C_{1-3}$-alkyl)amino-sulphonylamino, morpholin-4-yl-sulphonylamino, ($C_{1-3}$-alkylamino)thiocarbonylamino, ($C_{1-3}$-alkyloxy-carbonylamino)carbonylamino, arylsulphonylamino or aryl-$C_{1-3}$-alkyl-sulphonylamino group, d. an N—($C_{1-3}$-alkyl)-$C_{1-3}$-alkyl-carbonylamino, N—($C_{1-3}$-alkyl)-arylcarbonylamino, N—($C_{1-3}$-alkyl)-aryl-$C_{1-3}$-alkyl-carbonylamino, N—($C_{1-3}$-alkyl)-$C_{1-3}$-alkyloxy-carbonylamino, N-(aminocarbonyl)-$C_{1-3}$-alkylamino, N—($C_{1-3}$-alkyl-aminocarbonyl)-$C_{1-3}$-alkylamino, N-[di-($C_{1-3}$-alkyl)aminocarbonyl]-$C_{1-3}$-alkylamino, N—($C_{1-3}$-alkyl)-$C_{1-3}$-alkyl-sulphonylamino, N—($C_{1-3}$-alkyl)-arylsulphonylamino, or N—($C_{1-3}$-alkyl)-aryl-$C_{1-3}$-alkyl-sulphonylamino group, e. a 2-oxo-imidazolidin-1-yl, 2,4-dioxo-imidazolidin-1-yl or 2,5-dioxo-imidazolidin-1-yl group wherein the nitrogen atom in the 3 position may in each case be substituted by a methyl or ethyl group, f. a cyano, carboxy, $C_{1-4}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl or 4-($C_{1-3}$-alkyl)-piperazin-1-yl-carbonyl group, g. a $C_{1-3}$-alkyl-carbonyl or an arylcarbonyl group, h. a carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, piperazin-1-yl-carbonyl-$C_{1-3}$-alkyl or 4-($C_{1-3}$-alkyl)-piperazin-1-yl-carbonyl-$C_{1-3}$-alkyl group, i. a carboxy-$C_{1-3}$alkyloxy, $C_{1-3}$-alkyloxy-carbonyl-$C_{1-3}$-alkyloxy, cyano-$C_{1-3}$alkyloxy, aminocarbonyl-$C_{1-3}$alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyl-oxy, piperazin-1-yl-carbonyl-$C_{1-3}$alkyloxy or 4-($C_{1-3}$-alkyl)-piperazin-1-yl-carbonyl-$C_{1-3}$alkyloxy group, j. a hydroxy-$C_{1-3}$-alkyl, $C_{1-3}$alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, piperidin-1-yl-$C_{1-3}$-alkyl, morpholin-4-yl-$C_{1-3}$-alkyl, piperazin-1-yl-$C_{1-3}$-alkyl, 4-($C_{1-3}$-alkyl)-piperazin-1-yl-$C_{1-3}$-alkyl group, k. a hydroxy-$C_{1-3}$alkyloxy, $C_{1-3}$alkyloxy-$C_{1-3}$-alkyloxy, $C_{1-3}$-alkylsulphanyl-$C_{1-3}$alkyloxy, $C_{1-3}$-alkylsulphinyl-$C_{1-3}$-alkyloxy, $C_{1-3}$-alkylsulphonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)-amino-$C_{1-3}$-alkyloxy, pyrrolidin-1-yl-$C_{1-3}$-alkyloxy, piperidin-1-yl-$C_{1-3}$alkyloxy, morpholin-4-yl-$C_{1-3}$-alkyloxy, piperazin-1-yl-$C_{1-3}$-alkyloxy, 4-($C_{1-3}$-alkyl)-piperazin-1-yl-$C_{1-3}$-alkyloxy group, l. a mercapto, $C_{1-3}$-alkylsulphanyl, $C_{1-3}$-alkysulphinyl, arylsulphinyl, $C_{1-3}$-alkylsulphonyl, arylsulphonyl, $C_{1-3}$-alkylsulphonyloxy, arylsulphonyloxy, trifluoromethylsulphanyl, trifluoromethylsulphinyl or trifluoromethylsulphonyl group, m. a sulpho, aminosulphonyl, $C_{1-3}$-alkyl-aminosulphonyl, di-($C_{1-3}$-alkyl)-aminosulphonyl, pyrrolidin-1-yl-sulphonyl, piperidin-1-yl-sulphonyl, morpholin-4-yl-sulphonyl, piperazin-1-yl-sulphonyl or 4-($C_{1-3}$-alkyl)-piperazin-1-yl-sulphonyl group, n. a methyl or methoxy group substituted by 1 to 3 fluorine atoms, o. an ethyl or ethoxy group substituted by 1 to 5 fluorine atoms, p. a $C_{2-4}$-alkenyl or $C_{2-4}$-alkynyl group, q. a $C_{3-4}$-alkenyloxy or $C_{3-4}$-alkynyloxy group, r. a $C_{3-6}$-cycloalkyl or $C_{3-6}$-cycloalkyloxy group, s. a $C_{3-6}$-cycloalkyl-$C_{1-3}$-alkyl or $C_{3-6}$-cycloalkyl-$C_{1-3}$-alkyloxy group or t. an aryl, aryloxy, aryl-$C_{1-3}$-alkyl or aryl-$C_{1-3}$-alkyloxy group, ii. $R^{11}$ and $R^{12}$, which may be identical or different, in each case denote a fluorine, chlorine, bromine or iodine atom, a $C_{1-3}$-alkyl, trifluoromethyl, hydroxy or $C_{1-3}$-alkyloxy group or a cyano group, or iii. $R^{11}$ together with $R^{12}$, if they are bound to adjacent carbon atoms, also denote a methylenedioxy, difluoromethylenedioxy, straight-chain $C_{3-5}$-alkylene or —CH=CH—CH=CH— group, while the —CH=CH—CH=CH— group may be substituted by a fluorine, chlorine or bromine atom, by a methyl, trifluoromethyl, cyano, aminocarbonyl, aminosulphonyl, methylsulphonyl, methylsulphonylamino, methoxy, difluoromethoxy or trifluoromethoxy group, and iv. $R^{13}$ and $R^{14}$, which may be identical or different, in each case represent a fluorine, chlorine or bromine atom, a trifluoromethyl, $C_{1-3}$-alkyl or $C_{1-3}$-alkyloxy group, (b) a phenyl group which may be substituted by the groups $R^{10}$ to $R^{14}$, where $R^{10}$ to $R^{14}$ are as hereinbefore defined in this claim, (c) a phenyl-$C_{2-3}$-alkenyl group wherein the phenyl moiety may be substituted by the groups $R^{10}$ to $R^{14}$, where $R^{10}$ to $R^{14}$ are as hereinbefore defined in this claim, and the alkenyl group may be substituted by one to four fluorine atoms or methyl groups, while the substituents may be identical or different, (d) a phenyl-$C_{2-3}$-alkynyl group wherein the phenyl moiety may be substituted by the groups $R^{10}$ to $R^{14}$, where $R^{10}$ to $R^{14}$ are as hereinbefore defined in this claim, (e) a heteroaryl-$C_{1-6}$-alkyl group, while the $C_{1-6}$-alkyl group may be substituted by one to twelve fluorine atoms, (f) a heteroaryl group, (g) a heteroaryl-$C_{2-3}$-alkenyl group, while the alkenyl group may be substituted by one to four fluorine atoms or methyl groups, while the substituents may be identical or different, or (h) a heteroaryl-$C_{2-3}$-alkynyl group and (II) B denotes (a) an E-G group, wherein E is linked to the group A and
1. E denotes a. an oxygen or sulphur atom, b. an —$NR_a$— group wherein $R_a$ denotes a hydrogen atom, a $C_{1-6}$-alkyl, $C_{3-6}$-alkenyl, $C_{3-6}$-alkynyl, $C_{3-7}$-cycloalkyl, phenyl, phenylmethyl, heteroaryl, heteroarylmethyl, amino, $C_{1-6}$-alkylamino, di-($C_{1-6}$-alkyl)amino, hydroxy, $C_{1-6}$-alkyloxy group, while the above-mentioned phenyl rings may each be substituted by the groups $R^{10}$ to $R^{11}$, while $R^{10}$ to $R^{11}$ are as hereinbefore defined in this claim, c. an —$NR_a$—$NR_a$— group wherein $R_a$ is as hereinbefore defined in this claim and the two groups $R_a$ may be identical or different, d. an —NH—NH— group wherein the two hydrogen atoms are replaced by a straight-chain $C_{3-5}$-alkylene bridge, e. an —O—$NR_a$— group wherein $R_a$ is as hereinbefore defined in this claim and the oxygen atom is linked to the group A and the nitrogen atom is linked to the group G, f. a —O—$CR_bR_c$— group wherein the oxygen atom is linked to the group A and the carbon atom is linked to the group G and wherein $R_b$ and $R_c$, which may be identical or different, denote a hydrogen or fluorine atom, a $C_{1-6}$-alkyl, $C_{3-7}$-cycloalkyl, phenyl, phenylmethyl, while the phenyl rings may each be substituted by the groups $R^{10}$ to $R^{14}$, while $R^{10}$ to $R^{14}$ are as hereinbefore defined in this claim, or a heteroaryl or heteroaryl-methyl group or $R_b$ and $R_c$ together denote a straight-chain $C_{2-6}$-alkylene group, g. a —S—$CR_bR_c$— group wherein the sulphur atom is linked to the group A and the carbon atom is linked to the group G and $R_b$ and $R_c$, which may be identical or different, are as hereinbefore defined in this claim, h. a —SO—$CR_bR_c$— group wherein the sulphur atom is linked to the group A and the carbon atom is linked to the group G and $R_b$ and $R_c$, which may be identical or different, are as hereinbefore defined in this claim, i. a —$SO_2$—$CR_bR_c$— group wherein the sulphur atom is linked to the group A and the carbon atom is linked to the group G and $R_b$ and $R_c$, which may be identical or different, are as hereinbefore defined in this claim, j. or a —$NR_a$—$CR_bR_c$— group wherein the nitrogen atom is linked to the group A and the carbon atom is linked to the group G and $R_a$, $R_b$ and $R_c$, which may be identical or different, are as hereinbefore defined in this claim, and 2. G denotes
   a. a carbonyl or thiocarbonyl group,
   b. a methylene group substituted by an imino group wherein the nitrogen atom may be substituted by a $C_{1-6}$-alkyl, $C_{3-6}$-alkenyl, $C_{3-6}$-alkynyl, $C_{3-7}$-cycloalkyl, phenyl, phenylmethyl, heteroaryl, heteroarylmethyl, amino, $C_{1-6}$-alkylamino, di-$(C_{1-6}$-alkyl)amino, pyrrolidin-1-yl, piperidin-1-yl, morpholin-4-yl, $C_{1-6}$-alkyl-carbonylamino, phenylcarbonylamino, $C_{1-6}$-alkyloxy-carbonylamino, $C_{1-6}$-alkylsulphonylamino, phenylsulphonylamino, hydroxyl, $C_{1-6}$-alkyloxy, cyano or nitro group, while the above-mentioned phenyl groups may be substituted by the groups $R^{10}$ to $R^{14}$, where $R^{10}$ to $R^{14}$ are as hereinbefore defined in this claim,
   c. a 1,1-ethenylene group wherein the carbon atom in the exo position may be substituted by one or two chlorine or fluorine atoms or one or two $C_{1-6}$-alkyl, $C_{1-6}$-perfluoroalkyl, $C_{3-6}$-alkenyl, $C_{3-6}$-alkynyl, $C_{3-7}$-cycloalkyl, phenyl, phenylmethyl, heteroaryl, heteroarylmethyl, $C_{1-6}$-alkylcarbonyl, $C_{3-7}$-cycloalkyl-carbonyl, phenylcarbonyl, heteroarylcarbonyl, carboxy, $C_{1-6}$-alkyloxy-carbonyl, aminocarbonyl, $C_{1-6}$-alkylaminocarbonyl, di-$(C_{1-6}$-alkyl) aminocarbonyl, pyrrolidin-1-ylcarbonyl, piperidin-1-ylcarbonyl, morpholin-4-ylcarbonyl, phenylaminocarbonyl, heteroarylaminocarbonyl, $C_{1-6}$-alkylsulphinyl, $C_{3-7}$-cycloalkylsulphinyl, phenylsulphinyl, heteroarylsulphinyl, $C_{1-6}$-alkylsulphonyl, $C_{3-7}$-cycloalkylsulphonyl, phenylsulphonyl, heteroarylsulphonyl, cyano or nitro groups, while the substituents may be identical or different and the above-mentioned phenyl groups may be substituted by the groups $R^{10}$ to $R^{14}$, while $R^{10}$ to $R^{14}$ are as hereinbefore defined in this claim,
   d. or represent a sulphinyl or sulphonyl group,
(III) or A together with B denotes a 1,2,3,4-tetrahydroquinolinylcarbonyl, 1,2,3,4-tetrahydroisoquinolinylcarbonyl, 2,3-dihydroindolylcarbonyl or 2,3-dihydroisoindolylcarbonyl group wherein the benzo groups may in each case be substituted by the groups $R^{10}$ to $R^{13}$, while $R^{10}$ to $R^{13}$ are as hereinbefore defined in this claim and one or two carbon atoms of the benzo group may be replaced by nitrogen atoms and the alkylene moieties of the above-mentioned groups may in each case be substituted by one or two fluorine atoms, one or two methyl groups or an oxo group, while the substituents may be identical or different, and
(IV) D denotes
   (a) a $C_{1-6}$-alkylene group which may be substituted by one to twelve fluorine atoms,
   (b) a $C_{2-3}$-alkenylene group which may be substituted by one to four fluorine atoms or methyl groups,
   (c) or a propynylene group,
$R^2$ denotes
   (I) a hydrogen atom,
   (II) a $C_{1-6}$-alkyl group,
   (III) a $C_{2-4}$-alkenyl group,
   (IV) a $C_{3-4}$-alkynyl group,
   (V) a $C_{3-6}$-cycloalkyl group,
   (VI) a $C_{3-6}$-cycloalkyl-$C_{1-3}$-alkyl group,
   (VII) a tetrahydrofuran-3-yl, tetrahydropyran-3-yl, tetrahydropyran-4-yl, tetrahydrofuranylmethyl or tetrahydropyranylmethyl group,
   (VIII) an aryl group,
   (IX) an aryl-$C_{1-4}$-alkyl group,
   (X) an aryl-$C_{2-3}$-alkenyl group,
   (XI) an arylcarbonyl-$C_{1-2}$-alkyl group,
   (XII) a heteroaryl-$C_{1-3}$-alkyl group,
   (XIII) a furanylcarbonylmethyl, thienylcarbonylmethyl, thiazolylcarbonylmethyl or pyridylcarbonylmethyl group,
   (XIV) a $C_{1-4}$-alkyl-carbonyl-$C_{1-2}$-alkyl group,
   (XVI) a $C_{3-6}$-cycloalkyl-carbonyl-$C_{1-2}$-alkyl group,
   (XVII) an aryl-G-$C_{1-3}$-alkyl group, while G denotes an oxygen or sulphur atom, an imino, $C_{1-3}$-alkylimino, sulphinyl or sulphonyl group,
   (XVIII) a $C_{1-4}$-alkyl group substituted by a group $R_d$, wherein $R_d$ denotes a cyano, carboxy, $C_{1-3}$-alkyloxycarbonyl, aminocarbonyl, $C_{1-3}$-alkylamino-carbonyl, di-$(C_{1-3}$-alkyl)-amino-carbonyl, pyrrolidin-1-ylcarbonyl, piperidin-1-ylcarbonyl, morpholin-4-ylcarbonyl, piperazin-1-ylcarbonyl, 4-methylpiperazin-1-ylcarbonyl or 4-ethylpiperazin-1-ylcarbonyl group, or
   (XIX) a $C_{2-4}$-alkyl group substituted by a group $R_e$, where $R_e$ denotes a hydroxy, $C_{1-3}$-alkyloxy, amino, $C_{1-3}$-alkylamino, di-$(C_{1-3}$-alkyl)-amino, pyrrolidin-1-yl, piperidin-1-yl, morpholin-4-yl, piperazin-1-yl, 4-methyl-piperazin-1-yl or 4-ethyl-piperazin-1-yl group and is isolated from the cyclic nitrogen atom in the 3 position of the xanthine structure by at least two carbon atoms,
$R^3$ denotes
   (I) a $C_{3-8}$-alkyl group,
   (II) a $C_{1-3}$-alkyl group substituted by a group $R_f$, where $R_f$ denotes a $C_{3-7}$-cycloalkyl group optionally substituted by one or two $C_{1-3}$-alkyl groups or a $C_{5-7}$-cycloalkenyl group optionally substituted by one or two $C_{1-3}$-alkyl groups,
   (III) a $C_{3-8}$-alkenyl group,
   (IV) a $C_{3-6}$-alkenyl group substituted by a fluorine, chlorine or bromine atom or a trifluoromethyl group,
   (VI) a $C_{3-8}$-alkynyl group,
   (VII) an aryl group or
   (VIII) an aryl-$C_{2-4}$-alkenyl group,
and
$R^4$ denotes
   (I) an azetidin-1-yl or pyrrolidin-1-yl group which is substituted in the 3 position by an amino, $C_{1-3}$-alkylamino or a di-$(C_{1-3}$-alkyl)amino group and may additionally be substituted by one or two $C_{1-3}$-alkyl groups,
   (II) a piperidin-1-yl or hexahydroazepin-1-yl group which is substituted in the 3 position or in the 4 position by an amino, $C_{1-3}$-alkylamino or di-$(C_{1-3}$-alkyl) amino group and may additionally be substituted by one or two $C_{1-3}$-alkyl groups,
   (III) a 3-amino-piperidin-1-yl group wherein the piperidin-1-yl-moiety is additionally substituted by an aminocarbonyl, $C_{1-2}$-alkyl-aminocarbonyl, di-$(C_{1-2}$-alkyl)aminocarbonyl, pyrrolidin-1-yl-carbonyl, (2-cyano-pyrrolidin-1-yl)carbonyl, thiazolidin-3-ylcarbonyl, (4-cyano-thiazolidin-3-yl)carbonyl, piperidin-1-ylcarbonyl or morpholin-4-ylcarbonyl group,
   (IV) a 3-amino-piperidin-1-yl group wherein the piperidin-1-yl-moiety in the 4 position or in the 5 position is additionally substituted by a hydroxy or methoxy group,
   (V) a 3-amino-piperidin-1-yl group wherein the methylene group in the 2 position or in the 6 position is replaced by a carbonyl group, (VI) a piperidin-1-yl or hexahydroazepin-1-yl group substituted in the 3 position by an amino, $C_{1-3}$-alkylamino or di-($C_{1-3}$-alkyl)-amino group, wherein in each case two hydrogen atoms on the carbon skeleton of the piperidin-1-yl or hexahydroazepin-1-yl- group are replaced by a straight-chain alkylene bridge, this bridge containing 2 to 5 carbon atoms if the two hydrogen atoms are located on the same carbon atom, or 1 to 4 carbon atoms if the hydrogen atoms are located on adjacent carbon atoms, or 1 to 4 carbon atoms if the hydrogen atoms are located on carbon atoms separated by one atom, or 1 to 3 carbon atoms if the two hydrogen atoms are located on carbon atoms separated by two atoms, (VII) an azetidin-1-yl, pyrrolidin-1-yl, piperidin-1-yl or hexahydroazepin-1-yl group which is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, (VIII) a piperazin-1-yl or [1,4]diazepan-1-yl group optionally substituted on the carbon skeleton by one or two $C_{1-3}$-alkyl groups, while $R^4$ cannot represent a piperazin-1-yl or [1,4]diazepan-1-yl group optionally substituted on the carbon skeleton by one or two $C_{1-3}$-alkyl groups in those compounds wherein
  (a) the group E denotes an oxygen atom and the group G denotes a carbonyl group,
  (b) the group E denotes an oxygen atom and the group G denotes a sulphonyl group,
  (c) the group E denotes an —$NR_a$— group and the group G denotes a carbonyl group wherein $R_a$ is as hereinbefore defined in this claim,
  (d) the group E denotes an —$NR_a$— group wherein $R_a$ is as hereinbefore defined in this claim, and
  (e) the group G denotes a sulphonyl group or the group A denotes a phenyl or heteroaryl group optionally substituted by one of the above-mentioned groups and the group E denotes an oxygen atom and the group G denotes an ethenylene group, (IX) a 3-imino-piperazin-1-yl, 3-imino-[1,4]diazepan-1-yl or 5-imino-[1,4]diazepan-1-yl group optionally substituted on the carbon skeleton by one or two $C_{1-3}$-alkyl groups, (X) a [1,4]diazepan-1-yl group optionally substituted by one or two $C_{1-3}$-alkyl groups which is substituted in the 6 position by an amino group, (XV) a $C_{3-7}$-cycloalkylamino group wherein the cycloalkyl moiety is substituted by an amino, $C_{1-3}$-alkylamino or di-($C_{1-3}$-alkyl)-amino group, while the two nitrogen atoms on the cycloalkyl moiety are separated from one another by at least two carbon atoms, (XVI) an N—($C_{3-7}$-cycloalkyl)-N—($C_{1-3}$-alkyl)-amino group wherein the cycloalkyl moiety is substituted by an amino, $C_{1-3}$-alkylamino or di-($C_{1-3}$-alkyl)-amino group, while the two nitrogen atoms on the cycloalkyl moiety are separated from one another by at least two carbon atoms, (XVII) a $C_{3-7}$-cycloalkylamino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, (XVIII) an N—($C_{3-7}$-cycloalkyl)-N—($C_{1-3}$-alkyl)-amino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, (XIX) a $C_{3-7}$-cycloalkyl-$C_{1-3}$-alkyl-amino group wherein the cycloalkyl moiety is substituted by an amino, $C_{1-3}$-alkylamino or di-($C_{1-3}$-alkyl)-amino group, (XX) an N—($C_{3-7}$-cycloalkyl-$C_{1-2}$-alkyl)-N—($C_{1-2}$-alkyl)-amino group wherein the cycloalkyl moiety is substituted by an amino, $C_{1-3}$-alkylamino or di-($C_{1-3}$-alkyl)-amino group, (XXI) a $C_{3-7}$-cycloalkyl-$C_{1-2}$-alkyl-amino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, (XXII) an N—($C_{3-7}$-cycloalkyl-$C_{1-2}$-alkyl)-N—($C_{1-3}$-alkyl)-amino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, (XXIII) a $R^{19}$-$C_{2-4}$-alkylamino group wherein $R^{19}$ is separated from the nitrogen atom of the $C_{2-4}$-alkylamino moiety by at least two carbon atoms and $R^{19}$ denotes an amino, $C_{1-3}$-alkylamino or di-($C_{1-3}$-alkyl)-amino group, (XXIV) an $R^{19}$—$C_{2-4}$-alkylamino group wherein the nitrogen atom of the $C_{2-4}$-alkylamino moiety is substituted by a $C_{1-3}$-alkyl group and $R^{19}$ is separated from the nitrogen atom of the $C_{2-4}$-alkylamino moiety by at least two carbon atoms, while $R^{19}$ is as hereinbefore defined in this claim, (XXV) an amino group substituted by the group $R^{20}$ wherein $R^{20}$ denotes an azetidin-3-yl, azetidin-2-ylmethyl, azetidin-3-ylmethyl, pyrrolidin-3-yl, pyrrolidin-2-ylmethyl, pyrrolidin-3-ylmethyl, piperidin-3-yl, piperidin-4-yl, piperidin-2-ylmethyl, piperidin-3-ylmethyl or piperidin-4-ylmethyl group, while the groups mentioned for $R^{20}$ may in each case be substituted by one or two $C_{1-3}$-alkyl groups, or (XXVI) an amino group substituted by the group $R^{20}$ and a $C_{1-3}$-alkyl group wherein $R^{20}$ is as hereinbefore defined in this claim, while the groups mentioned for $R^{20}$ may in each case be substituted by one or two $C_{1-3}$-alkyl groups, while by the aryl groups mentioned in the definition of the above groups are meant phenyl or naphthyl groups, which may be mono- or disubstituted by $R_h$ independently of one another, where the substituents are identical or different and $R_h$ denotes a fluorine, chlorine, bromine or iodine atom, a trifluoromethyl, cyano, nitro, amino, aminocarbonyl, aminosulphonyl, methylsulphonyl, acetylamino, methylsulphonylamino, $C_{1-4}$-alkyl, $C_{1-3}$-alkyl-carbonyl, cyclopropyl, ethenyl, ethynyl, hydroxy, $C_{1-4}$-alkyloxy, $C_{1-4}$-alkoxy-carbonyl, methylsulphinyl, phenylsulphinyl, methylsulphonyl, phenylsulphonyl, difluoromethoxy or trifluoromethoxy group, by the heteroaryl groups mentioned in the definitions of the above-mentioned groups are meant a pyrrolyl, furanyl, thienyl, pyridyl, indolyl, benzofuranyl, benzothiophenyl, quinolinyl or isoquinolinyl group, or a pyrrolyl, furanyl, thienyl or pyridyl group wherein one or two methyne groups are replaced by nitrogen atoms, or an indolyl, benzofuranyl, benzothiophenyl, quinolinyl or isoquinolinyl group wherein one to three methyne groups are replaced by nitrogen atoms, or a 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 3,4-dihydro-4-oxo-quinazolinyl, 1,2,3,4-tetrahydro-2,4-dioxo-quinazolinyl, 1,2-dihydro-2-oxoquinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, cumarinyl, 2,3-dihydro-benzo[1,4]dioxinyl or 3,4-dihydro-3-oxo-2H-benzo[1,4]oxazinyl group, and the above-mentioned heteroaryl groups may be mono- or disubstituted by $R_h$, while the substituents may be identical or different and $R_h$ is as hereinbefore defined in this claim, and, unless otherwise stated, the above-mentioned alkyl, alkenyl and alkynyl groups may be straight-chain or branched, the tautomers, the enantiomers, the diastereomers, the mixtures thereof, and the salts thereof.

2. The compound of formula I according to claim 1, wherein $R^1$, $R^2$ and $R^3$ defined as in claim 1 and $R^4$ denotes (I) a pyrrolidin-1-yl group which is substituted in the 3 position by an amino group, (II) a piperidin-1-yl group which is substituted in the 3 position by an amino group, (III) a hexahydroazepin-1-yl- group which is substituted in the 3 position or in the 4 position by an amino group, (IV) a (2-aminocyclohexyl)amino group, or (V) an N-(2-aminoethyl)-N-methylamino or an N-(2-aminoethyl)-N-ethylamino group, while, unless otherwise mentioned, the above-mentioned alkyl, alkenyl and alkynyl groups may be straight-chain or branched, the tautomers, the enantiomers, the diastereomers, the mixtures thereof and the salts thereof.

3. The compound of formula I according to claim 2, wherein $R^1$ denotes an A-B-D group wherein A denotes a phenyl, phenylmethyl, 1-phenylethyl, pyridinyl, pyridinylmethyl, 1-pyridinylethyl, pyrimidinyl, pyrimidinylmethyl, pyrazinyl, pyrazinylmethyl, 1,3,5-triazinyl, 1,3,5-triazinylmethyl, 1,2,4-triazinyl, 1,2,4-triazinylmethyl, furanyl, thienyl, pyrrolyl, imidazolyl, 1,3-oxazolyl group, while the above-mentioned phenyl and heteroaryl groups may be substituted by a fluorine, chlorine or bromine atom or by a $C_{1-4}$-alkyl, $C_{1-4}$-alkoxy, trifluoromethyl, cyano, $C_{1-3}$-alkyl-carbonyl, $C_{1-4}$-alkoxy-carbonyl, methylsulphinyl, phenylsulphinyl, methylsulphonyl, phenylsulphonyl, amino or nitro group and may optionally additionally be substituted by a fluorine, chlorine or bromine atom or by a $C_{1-4}$-alkyl, $C_{1-4}$-alkoxy, trifluoromethyl or cyano group, while the substituents may be identical or different, and B denotes an E-G group wherein E is linked to the group A and E denotes an oxygen atom, an —NH—, —N(CH$_3$)— or —NH—NH— group or a —OCH$_2$-group wherein the oxygen atom is linked to the group A and the carbon atom is linked to the group G, and G denotes a carbonyl group, a cyanoiminomethylene or nitroiminomethylene group, or a 1,1-ethenylene group wherein the carbon atom in the exo position may be substituted by one or two trifluoromethyl, cyano, nitro, $C_{1-3}$alkyloxy-carbonyl, $C_{1-4}$-alkyl-carbonyl, phenylcarbonyl, $C_{1-3}$-alkylsulphinyl, phenylsulphinyl, $C_{1-3}$-alkylsulphonyl or phenylsulphonyl groups, while the substituents may be identical or different and the above-mentioned phenyl groups may be substituted by one or two fluorine, chlorine or bromine atoms or one or two $C_{1-3}$-alkyl, trifluoromethyl, $C_{1-3}$-alkoxy, cyano, $C_{1-3}$-alkyl-carbonyl, $C_{1-3}$-alkoxy-carbonyl, methylsulphinyl, phenylsulphinyl, methylsulphonyl, phenylsulphonyl or nitro groups, while these substituents may also be identical or different, or A and B together denote a 1,2,3,4-tetrahydroquinolin-1-ylcarbonyl or 1,2,3,4-tetrahydroisoquinolin-2-yl-carbonyl group and D denotes a methylene group, $R^2$ denotes a hydrogen atom or a $C_{1-3}$-alkyl group, $R^3$ denotes a $C_{4-6}$-alkenyl group, a 2-butyn-1-yl group, or a 1-cyclopenten-1-yl-methyl group, and $R^4$ denotes a piperidin-1-yl group which is substituted in the 3 position by an amino group, a hexahydroazepin-1-yl- group which is substituted in the 3 position or in the 4 position by an amino group, a (2-aminocyclohexyl) amino group, or an N-(2-aminoethyl)-N-methylamino or an aminoethyl)-N-ethylamino group, while, unless otherwise mentioned, the above-mentioned alkyl, alkenyl and alkynyl groups may be straight-chain or branched, the tautomers, the enantiomers, the diastereomers, the mixtures thereof and the salts thereof.

4. The compound of formula I according to claim 3, wherein $R^1$ denotes an A-B-D group wherein A denotes a phenyl, phenylmethyl, 1-phenylethyl, pyridinyl, pyridinylmethyl, 1-pyridinylethyl, pyrimidinyl or pyrimidinylmethyl group, where the phenyl moiety may be substituted by a fluorine, chlorine or bromine atom or by a $C_{1-4}$-alkyl, trifluoromethyl, $C_{1-4}$-alkoxy, cyano, $C_{1-3}$-alkyl-carbonyl, $C_{1-4}$-alkoxy-carbonyl, methylsulphinyl, phenylsulphinyl, methylsulphonyl, phenylsulphonyl, amino or nitro group and may optionally additionally be substituted by a fluorine, chlorine or bromine atom or by a $C_{1-4}$-alkyl, trifluoromethyl, $C_{1-4}$-alkoxy or cyano group, while the substituents may be identical or different, and B denotes a E-G group wherein E is linked to the group A and E denotes an oxygen atom, an —NH— group, —N(CH$_3$)— group or -OCH$_2$— group wherein the oxygen atom is linked to the group A and the carbon atom is linked to the group G, and G denotes a carbonyl group, or A and B together denote a 1,2,3,4-tetrahydroquinolin-1-ylcarbonyl or 1,2,3,4-tetrahydroisoquinolin-2-yl-carbonyl group and D denotes a methylene group, $R^2$ denotes a methyl group, $R^3$ denotes a 2-buten-1-yl, 3-methyl-2-buten-1-yl, or a 2-butyn-1-yl group and R⁴ denotes a (3-amino-piperidin-1-yl) group,
the tautomers, the enantiomers, the diastereomers, the mixtures thereof and the salts thereof.

5. The compound of formula I according to claim 4, wherein
R¹ denotes an A-B-D group wherein
A denotes a phenyl, phenylmethyl, pyridinyl or pyridinylmethyl group wherein the phenyl rings may be substituted by an amino, methoxy, methyl, cyano or nitro group, and
B denotes an E-G group wherein E is linked to the group A and
E denotes an oxygen atom, an —NH— group or —OCH₂— group wherein the oxygen atom is linked to the group A and the carbon atom is linked to the group G, and
G denotes a carbonyl group,
or A and B together denote a 1,2,3,4-tetrahydroquinolin-1-ylcarbonyl or 1,2,3,4-tetrahydroisoquinolin-2-ylcarbonyl group and
D denotes a methylene group,
R² denotes a methyl group,
R³ denotes a 2-buten-1-yl, 3-methyl-2-buten-1-yl or a 2-butyn-1-yl group
and
R⁴ denotes a (3-amino-piperidin-1-yl) group,
the tautomers, the enantiomers, the diastereomers, the mixtures thereof and the salts thereof.

6. The following compounds of formula I according to claim 1:
(a) 1-[(benzyloxycarbonyl)methyl]-3-methyl-7-(2-butyn-1-yl)-8-[(R)-3-amino-piperidin-1-yl]-xanthine,
(b) 1-[(benzylaminocarbonyl)methyl]-3-methyl-7-(2-butyn-1-yl)-8-[(R)-3-amino-piperidin-1-yl]-xanthine,
(c) 1-[(phenylaminocarbonyl)methyl]-3-methyl-7-(2-butyn-1-yl)-8-[(R)-3-amino-piperidin-1-yl]-xanthine,
(d) 1-{[(pyridin-2-yl)aminocarbonyl]methyl}-3-methyl-7-(2-butyn-1-yl)-8-[(R)-3-amino-piperidin-1-yl]-xanthine,
(e) 1-{[(pyridin-3-yl)methoxycarbonyl]methyl}-3-methyl-7-(2-butyn-1-yl)-8-[(R)-3-amino-piperidin-1-yl]-xanthine,
(f) 1-{[(pyridin-3-yl)aminocarbonyl]methyl}-3-methyl-7-(2-butyn-1-yl)-8-[(R)-3-amino-piperidin-1-yl]-xanthine,
(g) 1-{[(2-methyl-phenyl)aminocarbonyl]methyl}-3-methyl-7-(2-butyn-1-yl)-8-[(R)-3-amino-piperidin-1-yl]-xanthine,
(h) 1-{[(2-nitro-phenyl)aminocarbonyl]methyl}-3-methyl-7-(2-butyn-1-yl)-8-[(R)-3-amino-piperidin-1-yl]-xanthine,
(i) 1-{[(4-cyano-phenyl)aminocarbonyl]methyl}-3-methyl-7-(2-butyn-1-yl)-8-(3-amino-piperidin-1-yl)-xanthine,
(j) 1-{[(2-methoxy-phenyl)aminocarbonyl]methyl}-3-methyl-7-(2-butyn-1-yl)-8-[(R)-3-amino-piperidin-1-yl]-xanthine,
(k) 1-(2-oxo-3-phenoxy-propyl)-3-methyl-7-(2-butyn-1-yl)-8-(3-amino-piperidin-1-xanthine,
(l) 1-[(2-amino-benzylaminocarbonyl)methyl]-3-methyl-7-(2-butyn-1-yl)-8-(3-amino-piperidin-1-yl)-xanthine,
(m) 1-[2-(3,4-dihydro-1H-isoquinolin-2-yl)-2-oxo-ethyl]-3-methyl-7-(2-butyn-1-yl)-8-[(R)-3-amino-piperidin-1-yl]-xanthine,
(n) 1-[2-(3,4-dihydro-2H-quinolin-1-yl)-2-oxo-ethyl]-3-methyl-7-(2-butyn-1-yl)-8-[(R)-3-amino-piperidin-1-yl]-xanthine,
(o) 1-{[(3-cyano-phenyl)aminocarbonyl]methyl}-3-methyl-7-(2-butyn-1-yl)-8-(3-amino-piperidin-1-yl)-xanthine,
(p) 1-[(3-methoxy-benzyloxycarbonyl)methyl]-3-methyl-7-(2-butyn-1-yl)-8-[(R)-3-amino-piperidin-1-yl]-xanthine and (q) 1-[(3-nitro-benzyloxycarbonyl)methyl]-3-methyl-7-(2-butyn-1-yl)-8-[(R)-3-amino-piperidin-1-yl]-xanthine
and the salts thereof.

7. A pharmaceutical composition containing the compound according to any one of claims 1 to 6 together with one or more inert carriers and/or diluents.

8. A method comprising administering to a patient in need thereof a composition comprising the compound or physiologically acceptable salt thereof according to any one of claims 1 to 6 in an amount effective for the treatment of a disease or a condition selected from the group consisting of type II diabetes mellitus and obesity.

9. A process for preparing a pharmaceutical composition wherein the compound according to any one of claims 1 to 6 is incorporated in one or more inert carriers and/or diluents.

10. A process for preparing the compound of formula I according to claim 1 comprising the step of:
reacting a compound of formula II

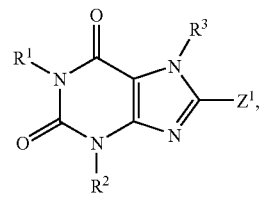

wherein
R¹ to R³ are defined as in claim 1 and
Z¹ denotes a leaving group,
with an amine of formula R⁴'—H, wherein R⁴' denotes one of the groups I to X or XV to XXVI of R⁴ in claim 1.

11. A method comprising administering to a patient in need thereof a compound according to one of claims 1 to 6 or a salt thereof in an amount effective for the treatment of type II diabetes mellitus.

12. A process for preparing the compound of formula I according to claim 1 comprising the step of deprotecting a compound of formula III

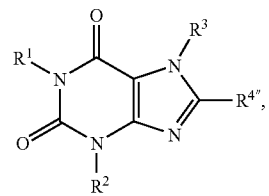

wherein R¹, R² and R³ are defined as in claim 1 and
R⁴'' denotes one of the groups mentioned for R⁴ hereinbefore that contains an imino, amino, or alkylamino group, wherein the imino, amino or alkylamino group is substituted by a protective group.

13. A method comprising administering to a patient in need thereof a compound according to one of claims 1 to 6 or a salt thereof in an amount effective for the prevention of a disease or a condition selected from the group consisting of type II diabetes mellitus and obesity.

14. A method of treating type II diabetes mellitus, or obesity, comprising administering to a patient in need thereof a pharmaceutically effective amount of a compound according to one of claims 1 to 6 or a tautomer, enantiomer, diastereomer or mixture thereof, or a salt thereof, wherein the administering is of 1 to 100 mg of the compound by intravenous route, or of 1 to 1000 mg by oral route, in each case 1 to 4 times a day.

15. A method of treating type II diabetes mellitus, or obesity, comprising administering to a patient in need thereof a pharmaceutically effective amount of a compound according to one of claims 1 to 6 or a tautomer, enantiomer, diastereomer or mixture thereof, or a salt thereof, wherein the administering is of 1 to 30 mg of the compound by intravenous route, or of 1 to 100 mg by oral route, in each case 1 to 4 times a day.

* * * * *